US008032347B2

(12) United States Patent
Reiner et al.

(10) Patent No.: US 8,032,347 B2
(45) Date of Patent: Oct. 4, 2011

(54) METHODS AND APPARATUS FOR PROTEIN SEQUENCE ANALYSIS

(75) Inventors: Neil E. Reiner, Vancouver (CA); Artem Tcherkassov, Vancouver (CA); Devki Nandan, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 1420 days.

(21) Appl. No.: 10/494,543

(22) PCT Filed: Nov. 1, 2002

(86) PCT No.: PCT/CA02/01632
§ 371 (c)(1),
(2), (4) Date: Oct. 27, 2004

(87) PCT Pub. No.: WO03/038724
PCT Pub. Date: May 8, 2003

(65) Prior Publication Data
US 2005/0112683 A1    May 26, 2005

Related U.S. Application Data

(60) Provisional application No. 60/349,371, filed on Jan. 22, 2002, provisional application No. 60/349,339, filed on Jan. 22, 2002, provisional application No. 60/393,385, filed on Jul. 5, 2002.

(30) Foreign Application Priority Data

Nov. 1, 2001  (CA) ..................................... 2360987

(51) Int. Cl.
G06F 7/00 (2006.01)
(52) U.S. Cl. ................ 703/12; 702/19; 702/20; 703/11; 435/6; 536/24.1
(58) Field of Classification Search ........................ None
See application file for complete search history.

(56) References Cited

U.S. PATENT DOCUMENTS

| | | | |
|---|---|---|---|
| 6,018,102 A | 1/2000 | Garbarino et al. | |
| 6,107,316 A | 8/2000 | Young et al. | |
| 6,127,524 A | 10/2000 | Casipit et al. | |
| 6,168,928 B1 | 1/2001 | Read et al. | |
| 6,268,160 B1 | 7/2001 | Clough et al. | |
| 6,306,663 B1 | 10/2001 | Kenten et al. | |
| 6,358,692 B1 | 3/2002 | Jindal et al. | |
| 6,541,008 B1 * | 4/2003 | Wise et al. | 424/198.1 |
| 6,645,747 B1 * | 11/2003 | Hallahan et al. | 435/193 |
| 7,572,589 B2 | 8/2009 | Reiner et al. | |
| 2003/0158672 A1 * | 8/2003 | Ramnarayan et al. | 702/19 |
| 2010/0151590 A1 | 6/2010 | Reiner et al. | |

FOREIGN PATENT DOCUMENTS

| | | |
|---|---|---|
| JP | 11318460 | 11/1999 |
| WO | WO 97/01578 | 1/1997 |

OTHER PUBLICATIONS

Higgins et al. (Methods in Enzymology vol. 266, pp. 383-402, 1996).*
Mott et al. Journal of Comuptational Biology vol. 6 No. 1, 1999.*
Taylor, WR. J Mol. Biol. 1997 269:902-943.*
Storey et al. J computational Biol. vol. 8 No. 5, 2001 p. 549-556.*
Hein et al. J Mol. Biol. 200 302:265-279.*
Aebischer, T., et al. Proteophosphoglycan, a major secreted product of intracellular Leishmania mexicana amastigotes, is a poor B-cell antigen and does not elicit a specific conventional CD4' T-cell response. Infect Immun (1999) 67(10):5379-5385.
Altschul, S.F., et al. Gapped BLAST and PSI-BLAST:a new generation of protein database search programs. Nucleic Acids Res. (1997) 25(17):3389-3402.
Andersen, G.R., et al. Crystal structures of nucleotide exchange intermediates in the eEF1A-eEF1Bα complex. Nat Struct Biol (2001) 8:531:534.
Aronov, A.M., et al. Rational design of selective submicromolar inhibitors of tritrichomonas foetus hypoxanthine-guanine-xanthine phosphoribosyltransferase. Biochemistry (2000) 39(18):4684-91.
Bairoch, A. and Apweiler R. The SWISS-PROT protein sequence database: its relevance to human molecular medical research. J Mol Med (1997) 75(5):312-316.
Bairoch, A. and Apweiler, R. The SWISS-PROT protein sequence database and its supplement TrEMBL in 2000. Nucleic Acid Res (2000) 28(1):45-48.
Baldauf, S.L., et al. Animals and fungi are each other's closest relatives: congruent evidence from multiple proteins. PNAS (1993) 90:11558-62.
Baldwin, G.C., et al. Human immunodeficiency virus causes mononuclear phagocyte dysfunction. Proc Nati Acad Sci USA (1990) 87:3933-3937.
Barral, A., et al. Transforming growth factor β as a virulence mechanism for *Leishmania braziliensis*. Proc Natl Acad Sci USA (1993) 90:3442-3446.
Basu, N., et al. Down-regulation of mannose receptors on macrophages after infection with *Leishmania donovani*. Biochem J (1991) 277 (Pt 2):451-456.
Beatty, W.L., et al. Identification of mycobacterial surface proteins released into subcellular compartments of infected macrophages. Infect Immun (2000)68(12):6997-7002.
Berg, K.L. et al. The major SHP-1-binding, tyrosine-phosphorylated protein in macrophages is a member of the KIR/LIR family and an SHP-1 substrate. Oncogene (1998) 17:2535-2541.
Beverley, S.M. Hijacking the cell: parasites in the driver's seat. Cell (1996) 87(5):787-789.
Binstadt, B.A., et al. SLP-76 is a direct substrate of SHP-1 recruited to killer cell inhibitory receptors. J Biol Chem (1998) 273(42):27518-27523.

(Continued)

Primary Examiner — Mary K Zeman
(74) Attorney, Agent, or Firm — Carol L. Francis; Bozicevic, Filed & Francis LLP

(57) ABSTRACT

Apparatus, methods, media, signals and data structures for protein sequence analysis are disclosed. A method includes identifying, from among a first group of aligned protein sequences having at least a threshold degree of alignment with a first protein sequence, a second group of at least one of the aligned sequences having at least one insertion or deletion ("indel") relative to the first protein sequence satisfying a predefined condition. The apparatus may include a processor circuit configured to carry out the method.

30 Claims, 9 Drawing Sheets

OTHER PUBLICATIONS

Figure 1:
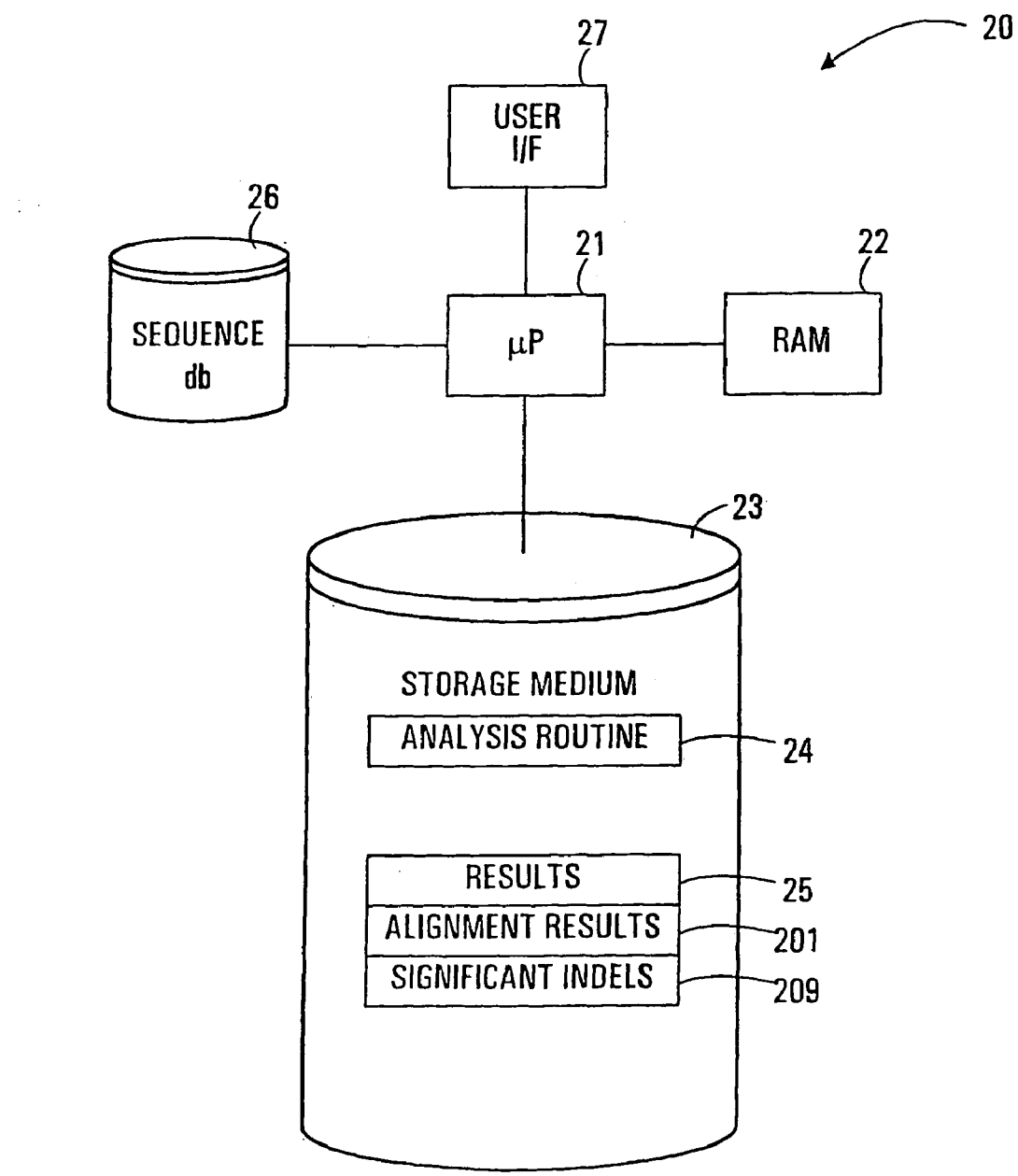

Blanchette, J., et al. Leishmania-induced increases in activation of macrophage SHP-1 tyrosine phosphatase are associated with impaired IFN-γ-triggered JAK2 activation. Eur J Immunol (1999) 29:3737-3744.

Blasioli, J., et al. Definition of the sites of interaction between the protein tyrosine phosphatase SHP-1 and CD22*. J Biol Chem (1999) 274(4):2303-2307.

Blery, M., et al. Early signaling via inhibitory and activating NK receptors. Hum Immunol (2000) 61:51-64.

Bliska, J.B., et al. Signal transduction in the mammalian cell during bacterial attachment and entry. Cell (1993) 73(5):903-920.

Bonafonte, M.T., et al. Isolation of the gene coding for elongation factor-1alpha in *Cryptosporidium parvum*. Biochim Blophys Acta (1997) 1351(3):256-60.

Borges, M.M., et al. Potent stimulation of the innate Immune system by a *Leishmania brasillensis* recombinant protein. Infect Immun (2001) 69(9):5270-7.

Bouchard, P., et al. Phosphorylation and Identification of a major tyrosine phosphorylation site in protein tyrosine phosphatase 1C*. J Biol Chem (1994) 269(30):19585-19589.

Bousquet, C., et al. sst2 somatostatin receptor mediates negative regulation of insulin receptor signaling through the tyrosine phosphatase SHP-1*. J Biol Chem (1998) 273(12):7099-7106.

Brummel, J.H., et al. Regulation of Src homology 2-containing tyrosine phosphatase 1 during activation of human neutrophlls. J Biol Chem (1997) 272(2):875-882.

Button, L.L., et al. Recombinant *Leishmania* surface glycoprotein GP63 is secreted in the *baculovirus* expression system as a latent metalloproteinase. Gene (1993) 134(1):75-81.

Carrero, J.C., et al. Cloning and characterization of Entamoeba histolytica antigens recognized by human secretory IgA antibodies. Parisitol Res (2000) 86(4):330-4.

Chan, J., et al. Lipoarabinomannan, a possible virulence factor involved in persistence of Mycobacterium tuberculosis within macrophages. Infect Immun (1991) 59(5):1755-1761.

Chen, H.E., et al. Regulation of colony-stimulating factor 1 receptor signaling by the SH2 domain-containing tyrosine phosphatase SHPTP1. Mol Cell Biol (1996) 16(7):3685-3897.

Ciechanover, A., et al. Ubiquitin-mediated proteolysis: biological regulation via destruction. Bioessays (2000) 22:442-451.

Clayton, C., et al. Protein trafficking in kinetoptastid protozoa. Microbiol Rev (1995) 59(3):325-344.

Clough, B., et al. Antibiotic inhibitors of organellar protein synthesis in *Plasmodium falciparum*. Protist (1999) 159(2):189-95.

Coggeshall, K.M. Negative signaling in health and disease. Immunol Res (1999) 19(1):47-64.

Cohen, G.B., et al. Modular binding domains in signal transduction proteins. Cell (1995) 80(2):237-248.

Colonna, M., et al. A novel family of Ig-like receptors of HLA class I molecules that modulate function of lymphoid and myeloid cells. J Leukoc Biol (1999) 68(3):375-381.

Condeelis, J. Elongation factor 1α, translation and the cytoskeleton. Trends Biochem Sci (1995) 20:169-170.

Damen, J.E., et al. Phosphorylation of tyrosine 503 in the erythropoietin receptor (EpR) is essential for binding the P85 subunit of phosphatidylinositol OPI) 3-kinase and for EpR-associated Pi 3-kinase activity. J Biol Chem (1995) 270:23402-23408.

Darnell, J.E., Jr., et al. Jak-STAT pathways and transcriptional activation in response to IFNs and other extracellular signaling proteins. Science (1994) 264(5164):1415-1421.

David, M., et al. Differential regulation of the alpha/beta interferon-stimulated Jak/Stat pathway by the SH2 domain-containing tyrosine phosphatase SHPTP1. Mol Cell Biol (1995) 15(12):7050-7058.

David, M., et al. The SH2 domain-containing tyrosine phosphatase PTP1D is required for interferon α/β gene expression. J Biol Chem (1996) 271(27)15862-15865.

Dell, K.R., et al. Stage-specific regulation of protein phosphorylation in *Leishmania major*. Mol Biochem Parasitol (1994) 64(2):283-292.

Denny, P.W., et al. Acylation-dependent protein export in *Leishmania*. J Biol Chem (2000) 275(15):11017-11025.

Descoteaux, A., et al. c-fos and tumor necrosis factor gene expression in *Leishmania donovani*-infected macrophages. Mol and Cell Biol (1989) 9(11):5223-5227.

Deshaies, R.J. SCF and Cullin/Ring H2-based ubiquitin ligases. Annual Review in Cellular Development Biology (1999) 15:435-467.

Dong, Q., et al. Negative regulation of myeloid cell proliferation and function by the SH2 domain-containing tyrosine phosphatase-1[1]. J Immunol (1999) 162:3220-3230.

Dustin, L.B., et al. Expression of dominant-negative Src-homology domain 2-containing protein tyrosine phosphatase-1 results in increased Syk tyrosine kinase activity and b cell activation J Immunol (1999) 182:2717-2724.

Eddy, S.R. Hidden markov models. Current Opinion in Structural Biology (1996) 6(3):361-365.

Edelsbrunner, H., et al. Measuring proteins and voids in proteins. In 28th International Conference on System Science. 1995. Hawaii.

Fantl, W.J., et al. Distinct phosphotyrosines on a growth factor receptor bind to specific molecules that mediate different signaling pathways. Cell (1992) 69(3):413-423.

Fastame, I.G., et al. Characterization of a novel translation inhibitor from *Leishmania* mexican promastigotes. Cell Mol Biol (1998) 44(3):475-81.

Fearon, D.T., et al. The instructive role of innate immunity in the acquired immune response. Science (1996) 272(5258):50-54.

Feng, G.S., et al. Phosphotyrosine phosphatases with SH2 domains: regulators of signal transduction. Trends Genet (1994) 10(2):54-58.

Feng, G.S., et al. SH2-containing phosphotyrosine phosphatase as a target of protein-tyrosine kinases. Science (1993) 259(5101):1607-1611.

Finbloom, D.S., et al. Regulation of the Jak/STAT signalling pathway. Cell Signal (1995) 7(8):739-745.

Finlay, B.B., et al. Exploitation of mammalian host cell functions by bacterial pathogens. Science (1997) 276(5313):718-725.

Forget, G., et al. Role of host phosphotyrosine phosphatase SHP-1 in the development of murine leishmaniasis, Eur J Immunol (2001) 31(11):3185-96.

Forget, G., et al. Progression of Leishmaniasis in SHP-1 deficient mice. Journal of Leukocyte Biology Supplement, 1999 Meeting Abstracts 31:133.

Frank, C., et al. Binding of phosphatidic acid to the protein-tyrosine phosphatase SHP-1 as a basis for activity modulation. Biochemistry (1999) 38(37):11993-12002.

Frearson, J.A. and Alexander, D.R. The role of phosphotyrosine phosphatases in haematopoietic cell signal transduction. Bioessays (1997) 19(5):417-427.

Fruth, U., et al. Leishmania major interferes with antigen presentation by infected macrophages. J Immunol (1993) 150(5):1857-1864.

Ganatra, J.B., et al. Viral causes of the acute retinal necrosis syndrome. Am J Ophthalmol (2000) 129:166-172.

Grädler, U., et al. A new target for shigellosis: rational design and crystallographic studies of inhibitors of tRNA-guanine transglycosylase. Journal of Molecular Biology (2001) 306(3):455-67.

Guex, N. and Peitsch, M.C. SWISS-MODEL and the Swiss-PdbViewer:an environment for comparative protein modeling. Electrophoresis (1997) 18:2714-2723.

Haque, S.J., et al. Receptor-associated constitutive protein tyrosine phosphatase activity controls the kinase function of JAK1. Proc Natl Acad Sci USA (1997) 94:8563-8568.

Haque, S.J., et al. Protein-tyrosine phosphatase Shp1-1 is a negative regulator of IL-4- and IL-13-dependent signal transduction. J Biol Chem (1998) 273(51):33893-33896.

Hmama, Z., et al. Attenuation of HLA-DR expression by mononuclear phagocytes infected with Mycobacterium tuberculosis is related to intracellular sequestration of immature class II heterodimers. J Immunol (1998) 161:4882-4893.

Hoedemaeker, F.J., et al. Crystal structure of the C-terminal sH2 domain of the P85α regulatory subunit of phosphoinositde 3-kinase: an SH2 domain mimicking its own substrate. J Mol Biol (1999) 292:763-770.

Horta, M.F. Pore-forming proteins in pathogenic protozoan parasites. Trends Microbiol (1997) 5(9):363-366.

Hunter, T. Protein kinases and phosphatases: the yin and yang of protein phosphorylation and signaling. Cell (1995) 80(2):225-236.

Ilg, T., et al. Characterization of phosphoglycan-containing secretory products of *Leishmania*. Parasitology (1994) 108 Suppl, S63-S71.

Imani, F., et al. Interleukin-4 (IL-4) induced phosphatidylinositol 3-kinase (p85) dephosphorylation. J Biol Chem (1997) 272(12):7927-7931.

Jiao, H., et al. Direct association with the dephosphorylation of Jak2 kinase by the Sh2-domain-containing protein tyrosine phosphatase SHP-1. Mol Cell Biol (1996) 16(12):6985-6992.

Jin, Y.J., et al. Human 70-kDa SHP-1L differs from 68-kDa SHP-1 in its C-terminal structure and catalytic activity. J Biol Chem (1999) 274(40):28301-28307.

Joiner, K.A. Perspectives series: host/pathogen Interactions. J Clin Invest (1997) 99(8):1814-1817.

Jones, D.T. Protein secondary structure prediction based on position-specific scoring matrices. J Mol Biol (1999) 292(2):195-202.

Joshi, P.B., et al. The gene encoding streptothricin acetyltransferase (sat) as a selectable marker for *Leishmania* expression vectors. Gene (1995) 156(1):145-9.

Joshi, P.L., et al. Targeted gene deletion of *Leishmania* major genes encoding developmental stage-specific leishmanolysin (GP63). Mol Microbiol (1998) 27(3):519-530.

Junker, V.L., et al. Representation of functional Information in the SWISS-PROT data bank. Bioinfomiatics (1999) 15(12): 1066-1007.

Kaur, K.J. and Ruben. Protein translation elongation factor-1α from Trypanosoma brucei binds Calmodulin. J Biol Chem (1994) 269:23045-23050.

Kaye, P.M., et al. Regulation of macrophage accessory cell activity by mycobacterial. II. In vitro inhibition of la expression by Mycobacterium microti. Clin Exp Immunol (1986) 64(1):28-34.

Kelly, J.M., et al. A shuttle vector which facilitates the expression of transfected genes in *Trypanosoma cruzi* and *Leishmania*. Nucleic Acids Research (1992) 20(15):3963-9.

Kharitonenkov, A., et al. A family of proteins that inhibit signalling through tyrosine kinase receptors. Nature (1997) 386(6621):181-186.

Kishimoto, A. et al. Studies on the phosphorylation of myelin basic protein by protein kinase C and adenosin 3':5'-monophosphate-dependent protein kinase. J Biol Chem (1985) 260:12492-12499.

Klingmuller, U., et al. Specific recruitment of sH-PTP1 to the erythropoietin receptor causes inactivation of JAK2 and termination of proliferative signals. Cell (1995) 80(5):729-738.

Knutson, K.L., et al. Lipoarabinomannan of mycobacterium tuberculosis promotes protein tyrosine dephosphorylation and inhibition of mitogen-activated protein kinase in human mononuclear phagocytes. J Biol Chem (1998) 273(1):645-652.

Kurogi, Y. and O.F. Guner. Pharmacophore modeling and three-dimensional database searching for drug design using catalyst. Curr Med Chem (2001) 8(9):1035-55.

Kwan, W.C., et al. Inhibition of expression of major histocompatibility complex class II molecules in macrophages infected with *Leishmania donovani* occurs at the level of gene transcription via a cyclic AM-Independent mechanism. Infect Immun (1992) 60(5):2115-2120.

Laban, A. and Wirth, D.F. Transfection of *Leishmania enriettii* and expression of chloramphenicol acetyltransferase gene. PNAS (1989) 86(23):9119-23.

Ladeira de Campos, C.B., et al. *Leishmania braziliansis*, molecular characterization of elongation factor-1alpha gene. Gene (1997) 198(1-2):281-8.

LeBowitz, J.H., et al. Development of a stable *Leishmania* expression vector and application to the study of parasite surface antigen genes. PNAS (1990) 87(24)9736-40.

Lesnick, M.L., et al. The Salmonella spvB virulence gene encodes an enzyme that ADP-ribosylates actin and destabilizes the cytoskeleton of eukaryotic cells. Mol Microbiol (2001) 39(6)1464-1470.

Long, E.O. Regulation of immune responses through inhibitory receptors. Annu Rv Immunol (1999) 17:875-904.

Lorenz, U., et al. Genetic analysis reveals cell type-specific regulation of receptor tyrosine kinase c-Kit by the protein tyrosine phosphatase SHP1. J Exp Med (1996) 184:1111-1126.

Marengere, L.E., et al. Regulation of T cell receptor signaling by tyrosine phosphatase SYP association with CTLA-4. Science (1996) 272(5265):1170-1173.

Matthews, R.J., et al. Characterization of hematopoietic intracellular protein tyrosine phosphatase: description of a phosphatase containing an SH2 domain and another enriched in proline-, glutamic acid-, seine-, and threonine-rich sequences. Mol Cell Biol (1992) 12(5):2396-2405.

Mendonca, S.M., et al. Identification of GTPase genesin the protozoa parasites *Trypanosoma cruzi* and *Leishmania amazonensis*. Biol Res (1993) 26(1-2):3-9.

Miranker, A., et al. Functionality maps of binding sites: a multiple copy simultaneous search method. Proteins: Structure, Function, and Genetics, 1991. 11:29-34.

Miskin, J.E., et al. A viral mechanism for inhibition of the cellular phosphatase calcineurin. Science (1998) 281(5376):562-565.

Murray, J.W., et al. Bundling of actin filaments by elongation factor 1α inhibits polymerization at filament ends. J Cell Biol (1996) 135:1309-1321.

Nandan, D., et al. Activation of phosphotyrosine phosphatase activity attenuates mitogen-activated protein kinase signaling and inhibits c-FOS and nitric oxide synthase expression in macrophages infected with *Leishmania donovani*. Infection and Immunity (1999) 67:4055-4063.

Nandan, D., et al. Exploitation of host cell signaling machinery:activation of macrophage phosphotyrosine phosphatases as a novel mechanism of molecular microbial pathogenesis. J Leukocyte Biology (2000) 67:464-470.

Nandan, D. and Reiner N.E. Attenuation of gamma interferon-induced tyrosine phosphorylation in mononuclear phagocytes infected with *Leishmania donovani*: selective inhibition of signaling through Janus kinases and Stat1. Infect Immun (1995) 63(11)4495-4500.

Nandan, Devki, et al. *Leishmania* EF-1α activates the Src homology 2 domain containing tyrosine phosphatase SHP-1 leading to macrophage deactivation. The Journal of Biochemistry. (2002) 277(51): 50190-50197. XP-002232633.

Needleman, S.B. and Wunsch, C.D. A general method applicable to the search for similarities in the amino acid sequence of two proteins. Journal of Molecular Biology (1970) 48(3):443-453.

Nitschke, L., et al. CD22 is a negative regulator of B-cell receptor signalling. Curr Biol (1997) 7(2):133-143.

Olivier, M., et al. Modulation of interferon-γ-induced macrophage activation by phosphotyrosln phosphatases inhibition. J Biol Chem (1998) 273:13944-13949.

Olivier, M., et al. Defective stimulus-response coupling in human monocytes infected with *Leishmania donovani* is associated with altered activation and translocation of protein kinase C. Proc Natl Acad Sci SA (1992) 89:7481-7485.

Olivier, M., et al. Stimulus-response coupling in monocytes infected with *Leishmania*. Attenuation of calcium transients is related to defective agonist-induced accumulation of inositol phosphates. J Immunol (1992) 148(4)1188-1196.

Ono, M., et al. Deletion of SHIP or SHP-1 reveals two distinct pathways for inhibitory signaling. Cell (1997) 90(2):293-301.

Ooms, F. Molecular modeling and computer aided drug design. Examples of their applications in medicinal chemistry. Current Medicinal Chemistry (2000) 7(2):141-58.

Pathak, M.K and Yi, T. Sodium stibogluconate is a potent inhibitor of protein tyrosine phosphatases and augments cytokine responses in hemopoietic cell lines. J Immunol (2001) 167(6):3391-3397.

Pawson, T. Protein modules and signalling networks. Nature (1995) 373(6515):573-580.

Pei, D., et al. Differential functions of the two Src homology 2 domains in protein tyrosine phosphatase SH-PTP1. Proc Natl Acad Sci USA (1998) 93:1141-1145.

Perkins, L.A., et al. Corkscrew encodes a putative protein tyrosine phosphatase that functions to transduce the terminal signal from the receptor tyrosine kinase torso. Cell (1992) 70(2):225-236.

Piani, A., et al. *Leishmania* major proteophosphoglycan is expressed by amastigotes and has an immunomodulatory effect on macrophage function. Microbes Infect (1999) 1(8):589-599.

Pinna, L.A. Casein kinase 2:an 'eminence gris' in cellular regulation? Biochim Biophys Acta (1990) 1054(3):267-284.

Plutzky, J., et al. Isolation of a src homology 2-containing tyrosine phosphatase. Proc Nat Acad Sci (1992) 89:1123-1127.

Reiner, N.E., Altered cell signaling and mononuclear phagocyte deactivation during Intracellular infection. Immunol. Today (1994) 15:374-381.

Reiner, N.E. Host-parasite relationship in murine leishmaniasis: pathophysiological ad immunological changes. Infect Immun (1982) 38:1223-1230.

Reiner, N.E., et al. Kinetics of γ Interferon binding and induction of major histocompatibility complex class II mRNA in Leishmania-infected macrophages. Proc Natl Acad Sci (1988) 85:4330-4334.

Reiner, N.E., et al. Modulation of in vitro monocyte cytokine responses to *Leishmania donovani*. J Clin Invest (1990) .85:1914-1924.

Reiner, N.E., et al. Arachidonic acid metabolism by murine peritoneal macrophage infected with *Leishmania donovani*: in vitro evidence for parasite-induced alterations in cyclooxygenase and lipoxygenase pathways. J Immunol (1985) 134(1):556-563.

Rey-Ladino, J.A., et al. Expression of 65- and 67-kilodalton heat-regulated proteins and a 70-kilodalton heat shock cognate protein of *Leishmania donovani* in macrophages. Infect Immun (1993) 61(8):3265-3272.

Rey-Ladino, Jose A., et al. *Leishmania* major: molecular cloning, sequencing, and expression of the heat shock protein 60 gene reveals unique carboxy terminal peptide sequences. Experimental Parasitology. (1997) 85(3): 249-263. XP002232632 ISSN 0014-4894.

Ridgley, E.L., et al. Genomic organization and expression of elongation factor-1α genes in Trypanosoma brucei. Molecular and Biochemical Parasitology (1996) 79:119-123.

Rost, B. and Sander C., Prediction of protein secondary structure at better than 70% accuracy. J Mol Biol (1993) 232(2):584-599.

Rost, B. and Sander, C. Improved prediction of protein secondary structure by use of sequence profiles and neural networks. Proc Natl Acad Sci USA (1993) 90(16):7558-62.

Rost, B. and Sander, C. Combining evolutionary information and neural networks to predict protein secondary structure. Proteins:Structure, Function and Genetics (1994) 19(1):55-72.

Sakamoto, K.M., et al. Protacs: chimeric molecules that target proteins to the Skp1-cullin-F box complex for ubiquitination and degradation. PNAS (2001) 98(15):8554-9.

Schaible, U.E., et al. Parasitophorous vacuoles of *Leishmania mexicana* acquire macromolecules from the host cell cytosol via two independent routes. J Cell Sci (1999) 112 (pt 5):681-693.

Servidei, T., et al. Coordinate regulation of STAT signaling and c-fos expression by the tyrosine phosphatase SHP-2*. J Biol Chem (1998) 273(11):6233-6241.

Shen, S.H., et al. A protein-tyrosine phosphatase with sequence similarity to the SH2 domain of the protein-tyrosine kinases. Nature (1991) 352(6337):736-739.

Shultz, L.D., et al. Severe defects in immunity and hematopoiesis caused by SHP-1 protein-tyrosine-phosphatase deficiency. Trends Biotechnol (1997) 15(8):302-307.

Shultz, L.D., et al. Mutations at the murine motheaten locus are within the hematopoietic cell protein-tyrosine phosphatase (Hcph) gene. Cell (1993) 73(7):1445-1454.

Shultz, L.D. Pleiotropic effects of deleterious alleles at the "motheaten" locus. Curr Top Microbiol Immunol (1988) 137:216-222.

Sibley, L.D., et al. Mycobacterium leprae-burdened macrophages are refractory to activation by gamma interferon. Infect Immun (1987) 55(2):446-450.

Sibley, L.D et al. Inhibition of interferon-gamma-mediated activation in mouse macrophages treated with lipoarabinomannan. Clin Exp Immunol (1990) 80(1):141-148.

Siegal, G., et al. Solution structure of the C-terminal SH2 domain of the p85 alpha regulatory subunit of phosphoinositide 3-kinase. J Mol Biol (1998) 276:461-478.

Smith, T.F. and Waterman, M.S., Identification of common molecular subsequences. Journal of Molecular Biology (1981) 147(1):195-197.

Somani, A.K., et al. Src kinase activity is regulated by the SHP-1 protein-tyrosine phosphatase. J Biol Chem (1997) 272(34):21113-21119.

Sonnenberg, M.G., et al. Definition of Mycobacterium tuberculosis culture filtrate proteins by two-dimensional polyacrylimide gel electrophoresis, N-terminal amino acid sequencing, and electrospray mass spectrometry. Infect Immun (1997) 65(11):4515-4524.

Songyang, Z., et al. SH2 domains recognize specific phosphopeptide sequences. Cell (1993) 72(5):767-778.

Stein, R.C. and Waterfield, M.D. PI3-kinase inhibition: a target for drug development? Mol Med Today (2000) 6:347-357.

Su, L, et al. Positive effect of overexpressed protein-tyrosine phosphatase PTP1C on mitogen-activated signaling in 293 cells* . J Biol Chem (1996) 271(17):10385-10390.

Tabrizi, M., et al. Reduced Tyk2/SHP-1 interaction and Icak of SHP-1 mutation in a kindred of familial hemophagocytic lymphohistiocytosis. Leukemia (1998) 12(2):200-206.

Tellam, J., et al. Targeting of EBNA1 for rapid intracellular degradation overrides the inhibitory effects of the Gly-Ala repeat domain and restores CD8+ T cell recognition. Journal of Biological Chemistry (2001) 276(36):33353-60.

Tonks, N.K. , et al. From form to function: signaling by protein tyrosine phosphatases. Cell (1996) 87(3):365-368.

Tsui, H.W., et al. Motheaten and viable motheaten mice have mutations in haematopoietic cell phosphatase gene. Nature Genet (1993) 4(2)124-9.

Turco, S.J., et al. The lipophosphoglycan of *Leishmania* parasites. Annu Rev Microbiol (1992) 46:65-94.

Uchida, T., et al. Insulin stimulates the phosphorylation of Tyr$^{538}$ and the catalytic activity of PTP1C, a protein tyrosine phosphatase with Src homology-2 domains*. J Biol Chem (1994) 269(16):12220-12228.

Vanhaesenbroeck, B., et al. Distinct PI(3)Ks mediate mitogenic signalling and cell migration in macrophages. Nat Cell Biol (1999) 1:69-71.

Veillette, A., et al. High expression of inhibitory receptor SHPS-1 and its association with protein-tyrosine phosphatase SHP-1 in macrophages* . J Biol Chem (1998) 273(35):22719-22728.

Vinkenoog, R., et al. Malaria parasites contain two identical copies of an elongation factor 1 alpha gene. Mol Biochem Parasitol (1998) 94(1);1-12.

Wang, L.L., et al. Specificity of the SH2 domains of SHP-1 in the interaction with the immunoreceptor tyrosine-based inhibitory motif-bearing receptor gp49B' J Immunol (1999) 162:1318-1323.

Webb, J.R., et al. *Leishmania* major HEXBP deletion mutants generated by double targeted gene replacement. Mol Biochem Parasitol (1994) 63(2):231-242.

Weldingh, K., et al. Two-dimensional electrophoresis for analysis of mycobacterium tuberculosis culture filtrate and purification and characterization of six novel proteins. Infection and Immunity (1998) 66(8):3492-3500.

Yeremeev, V.V., et al. The 19-dK antigen and protective immunity in a murine model of tuberculosis. Clin Exp Immunol (2000)120:274-279.

Yetter, A., et al. Association of the interferon-dependent tyrosine kinase Tyuk-2 with the hematopoietic cell phosphatase. J Biol Chem (1995) 270(31):18179-18182.

Yi, T. et al. Hematopoietic cell phosphatase associates with the interleukin-3 (IL-3_receptor β chain and down-regulates IL-3-induced tyrosine phosphorylation and mitogenesis. Mol Cell Biol (1993) 13(12):7577-7586.

Yi, T., et al. Protein tyrosine phosphatase containing SH2 domains: characterization , preferential expression in hematopoietic cells, and localization to human chromosome 12p12-p13. Mol Cell Biol (1992) 12(2):836-846.

Yohannan, J., et al. Analysis of tyrosine phosphorylation-dependent interactions between stimulatory effector proteins and the B cell co-receptor CD22. J Biol Chem (1999) 274:18769-18776.

You, M., et al. Positive effects of SH2 domain-containing tyrosine phosphatase SHP-1 on epidermal growth factor-1 and interferon-γ-stimulated activation of STAT transcription factors in HeLa cells. J Biol Chem (1997) 272(37):23376-23381.

You, M., et al. Shp-2 tyrosine phosphatase functions as a negative regulator of the interferon-stimulated Jak/STAT pathway. Mol Cell Biol (1999) 19(3):2416-2424.

Zhang, Z.Y. Protein-tyrosine phosphatases: biological function, structural characteristics, and mechanism of catalysis. Crit Rev Biochem Mol Biol (1998) 33(1):1-52.

Office Action mailed Jun. 19, 2007 in U.S. Appl. No. 10/494,175.

Billaut-Mulot, O., et al. *Trypanosoma cruzi* elongation factor 1-alpha gene. Database accession No. L76077 XP002232636 Published Sep. 26, 1996.

Brands, J.G.H. M., et al. Elongation factor 1-alpha 1' Database accession No. P04720 XP002232634 Published Aug. 13, 1987.

De Meester, F, et al. Entamoeba histolytica elongation factor-1 alpha' Database accession No. M92073 XP002232637 Published Jan. 1991.

Hashimoto, T. G.lamblia mRNA elongation factor 1-alpha, partial cds. Database accession No. D14342 XP002232640 Submitted Feb. 2, 1993.

Mead, J.R., et al. Cryptosporidium parvum elongation factor 1-alpha (EF-1 alpha). Database accession No. 069697 XP002232639 Submitted Sep. 5, 1996.

Nandan, D.E., et al. *Leishmania donovani* elongation factor 1-alpha mRNA, partial cds. Database accession No. AF416379 XP002232635 Submitted Sep. 2, 2001.

Williamson, D.H. *P. falciparum* MEF-1 gene for EF-1 alpha elongation factor' Database accession No. X60488 XP002232638 Submitted Jun. 4, 1991.

Bowie, J.U., et al. Deciphering the Message in Protein Sequences: Tolerance to Amino Acid Substitutions, *Science*, vol. 247, pp. 1306-1310, Mar. 16, 1990.

Greenspan, N.S. & Di Cera, B., Defining epitopes: It's not as easy as it seems, *Nature Biotechnology*, vol. 17, pp. 936-937, Oct. 1999.

Holmes, E.H., PSMA specific antibodies and their diagnostic and therapeutic use, *Exp.Opin.InVest.Drugs* (2001) 10(3): 511-519.

Rudinger, J., Characteristics of the amino acids as components of a peptide hormone sequence, in Peptide Hormones edited by Parsons, J.A., University Park Press, Jun. 1976.

Kamaishi et al., "Protein Phylogeny of Translation Elongation Factor EF1a Suggests Microsporidians are Extremely Ancient Eukaryotes" Journal of Molecular Evolution (1996) 42:257-263.

Kamla et al., "Species Differentiation of Mycoplasmas by EF-Tu Specific Monoclonal Antibodies" Journal of Immunological Methods 147 (1992) 73-81.

Stuart M. "An Antibody Diagnostic for Hymenopteran Parasitism is Specific for a Homologue of Elongation Factor-1a" Archives of Insect Biochemistry and Physiology 39:1-8 (1998).

Billaut-Mulot, et al. (1996) "*Trypanosoma cruzi* Elongation Factor 1-α: Nuclear Localization in Parasites Undergoing Apoptosis" Gene. 174 :19-26.

Gao, et al. (2005) "Conserved Indels in Protein Sequences that are Characteristic of the Phylum Actinobacteria" International J. of Systematic and Evolutionary Microbiology. 55:2401-2412.

Griffiths, et al. (2005) "Conserved Indels in essential Proteins that are distinctive Characteristics of Chlamydiales and Provide Novel Means for Their Identification" Microbiology. 151:2647-2657.

Gupta (2004) "The Outlines of Bacterial Evolution" Origins: Genesis, Evolution and Diversity of Life. Ed. Joseph Seckbach. 266-279.

Gupta, et al. (2006) "Chlamydiae-Specific Proteins and Indels: Novel Tools for Studies" Trends in Microbiology. 14 (12):527-535.

Lederman, et al. (1991) "A Single Amino Acid Substitution in a Common African Allele of the CD4 Molecule Ablates Binding of the Monoclonal Antibody, OKT4" Molecular Immunology. 28(11):1171-1181.

Li, et al. (1980) "β-Endorphin Omission Analogs: Dissociation of Immunoreactivity from other Biological Activities" Proc. Natl. Acad. Sci. USA. 77(6):3211-3214.

* cited by examiner

Query= AC010491.3.1.141706.4 ~902
      (462 letters)

P90632 ELONGATION FACTOR EF-1A. ~904
      Length = 447
  Organism: Leishmania braziliensis.

Score =  627 bits (1616), Expect = e-179
  Identities = 307/432 (71%), Positives = 351/432 (81%), Gaps = 13/432 (3%)

Query:   1  MGKEKTHINIVVIGHVDSGKSTTTGHLIYKCSSIDKRTIEKFEKETAEMGKGSFKYGWVL  60
            MGK+K H+N+VV+GHVD+GKST TGHLIYKC  IDKRTIEKFEKE AEMGK SFKY WVL
Sbjct:   1  MGKDKVHMNLVVVGHVDAGKSTATGHLIYKCGGIDKRTIEKFEKEAAEMGKASFKYAWVL  60

Query:  61  DKLKAERERGITIDISLWKFETSKYYVTIITDAPGHRDFIKNMITGTSQADCAVPIVAAGV  120
            DKLKAERERGITIDI+LWKFE+ K   TI DAPGHRDFIKNMITGTSQAD A+  + +
Sbjct:  61  DKLKAERERGITIDIALWKFESPKSVFTIIDAPGHRDFIKNMITGTSQADAAILMIDSTQ  120

Query: 121  GEFEAGISKNGQTREHALLAYTLGVKQLIVGVNKMDSTEPPYSQKRYEEIVKEVSTYIKK  180
            G FEAG+SK+GQTREHALLA+TLGVKQ++V  NKMD    YSQ RYEEI KEV TY+K+
Sbjct: 121  GGFEAGVSKDGQTREHALLAFTLGVKQMVVCNKMDDKTVQYSQARYEEISKEVGTYLKR  180

Query: 181  IGYNPDTVAFVPISGWNGNNMLEPSANMPWFKGWKVTRKDGNASGTMLLEALDCILPPTR  240
            +GYNP+ V F+PISGW G+NM++  S +M W+K           G LL+ALD +    R
Sbjct: 181  VGYNPEKVRFIPISGWQGDNMIDKSESMAWYK-----------GPTLLDALDMLAGAVR  228

Query: 241  PTDKPLRLPLQDVYKIGGIGSVPVGRVETGILKPGMVVTFAPVNVTTEVKSVEMHHEALG  300
            P DKP    P DVYKIGGIG+VPVGRVETGI+KPG VVTFAP NVTTEVKS+EMHHE L
Sbjct: 229  PVDKPGAAP-ADVYKIGGIGTVPVGRVETGIMKPGDVVTFAPANVTTEVKSIEMHHEQLA  287

Query: 301  EALPGDSVGFHVKNVSVKDVRRGNVAGDSKNDPPMEAAGFTAQVIILNHPGQISAGYAPV  360
            EA+PGD+VGF+VKNVSVKD+RRGNV G+SKNDP  E A FTAQVI+LNHPGQIS GYAPV
Sbjct: 288  EAVPGDNVGFNVKNVSVKDIRRGNVWGNSKNDPAEEPADFTAQVIVLNHPGQISNGYAPV  347

Query: 361  LDCHTAHIACKFAELKEKIDRRSGKKLEDGPKFLKSGDAAIVDMVPGKPMCAESFSDYPP  420
            LDCHT+HIAC+F  ++ KIDRRSGK +E  PK +KSGDAAIV MVP KPMC E F+DYPP
Sbjct: 348  LDCHTSHIACRFGTIESKIDRRSGKDVEKNPKAIKSGDAAIVKMVPQKPMCVEVFNDYPP  407

Query: 421  LGRFAVRDMRHT  432
            LGRFAVRDMR T
Sbjct: 408  LGRFAVRDMRRT  419

FIG. 9

METHODS AND APPARATUS FOR PROTEIN SEQUENCE ANALYSIS

CROSS-REFERENCE TO RELATED APPLICATIONS

This application claims the benefit of priority from Canadian patent application serial no. 2,360,987 filed Nov. 1, 2001; U.S. patent application Ser. No. 60/349,339 filed Jan. 22, 2002; U.S. patent application Ser. No. 60/349,371 filed Jan. 22, 2002; and U.S. patent application Ser. No. 60/393,385 filed Jul. 5, 2002.

FIELD OF THE INVENTION

The present invention relates to sequence analysis, and more particularly, to apparatus, methods, computer-readable media, computer programs, signals and data structures for protein sequence analysis.

BACKGROUND OF THE INVENTION

Methods are known for comparing the amino acid sequences of proteins to identify indel (insertion/deletion) associated sequences. Such methods are described for use in identifying peptides, peptide analogs, and peptidomimetics that have a high probability of modulating or mimicking the activity of a target protein. For example, in PCT international patent application publication no. WO 97/01578, methods are described for identifying molecules that affect biological activity of a target protein in which information regarding the location of an indel in a target protein is used to identify nearby fragments.

Protozoan pathogens are responsible for a wide variety of disease, typically tropical in nature. These pathogens exist as intracellular parasites in a host and include organisms that appear to be protozoan in nature such as *Pneumocystis*. An example of such protozoan pathogens is the genus *Leishmania*, which causes a spectrum of tropical and subtropical diseases known as the leishmaniases. These consist of several forms including cutaneous, mucocutaneous, visceral and diffuse cutaneous leishmaniasis. The incidence of such tropical diseases has been on the rise due to multiple factors including the AIDS epidemic, increased international travel, lack of effective vaccines, difficulty in controlling vectors, and the development of resistance to chemotherapy.

*Leishmania* live as either extracellular, flagellated promastigotes in the digestive tract of their sand fly vector or as non-flagellated amastigotes within macrophages where they survive and replicate within phagolysosomes. During both the innate and acquired immune responses, macrophages respond to extracellular signals to become activated for enhanced antimicrobial activity. This is a critical requirement leading to the elimination of intracellular pathogens. However, recent findings have shown that *leishmania* and other intracellular pathogens have developed mechanisms to interfere with cell signaling pathways thereby preventing macrophages from becoming effectively activated [Reiner N E. (1994) *Immunol. Today* 15:374-381; Nandan, D. et al. (2000) *J Leukocyte Biology* 67:464-470]. As a result, these organisms are able to survive and successfully multiply within the otherwise hostile intracellular milieu of macrophages. *L. donovani* is the major causative agent of human visceral leishmaniasis. This disease is progressive and often fatal if untreated. Recently, it has been shown that macrophages infected with *L. donovani* show a phenotype of impaired cell signaling and cell deactivation. For example, interferon-γ signaling through the Jak-Stat1 pathway [Nandan D. and Reiner N E. (1995) *Infect. Immun.* 63:4495-4500] and mitogen-activated protein kinase signaling leading to iNOS induction and c-FOS expression were observed to be markedly attenuated in *leishmania* infected cells [Nandan D. et al. (I 999) *Infection and Immunity* 67:4055-4063]. Of significant interest was the finding that the deactivated phenotype was reversed in cells that had been incubated with the protein tyrosine phosphatase (PTP) inhibitor sodium orthovandate prior to infection [Nandan D. et al. (1999) *Infection and Immunity* 67:4055-4063]. Several lines of evidence have recently converged to demonstrate a role for the Src-homology 2 (SH2) domain containing protein tyrosine phosphatase-1 (SHP-1) in the pathogenesis of infections with *leishmania* [Nandan D. et al. (1999) *Infection and Immunity* 67:4055-4063; Olivier M. et al. (1998) *J. Biol. Chem.* 273: 13944-13949; Blanchette J. et al. (1999) *Eur. J Immunol.* 29:3737-3744; Forget G. et al. (1999) *Journal of Leukocyte Biology Supplement* 31:1999]. In particular, SHP-1 has been shown to become activated in *leishmania* infected cells [Nandan D. et al. (1999) *Infection and Immunity* 67:4055-4063; 6] and *leishmania* infection is attenuated under conditions of SHP-1 deficiency [Forget G. et al. (1999) *Journal of Leukocyte Biology Supplement* 31:1999]. Moreover, it has recently been shown that a conventional anti-leishmanial agent used clinically, sodium stibogluconate, is an inhibitor of SHP-1 [Pathak M K. and Yi T. (2001) *J Immunol.* 167:3391-3397].

SUMMARY OF THE INVENTION

It was surprising to discover that essential pathogen proteins can contain insertions or deletions compared to their host homologues conferring structural differences that may be exploited as drug targets specific for the pathogen. Proteins that are essential to pathogen survival can contain discrete, heretofore unrecognized indels which differentiate them from their otherwise highly related mammalian homologues. Up to now, because of their high degree of relatedness and because many of the host proteins were essential for survival of both the host and the pathogen, these proteins have not been candidate drug targets.

In accordance with one aspect of the invention, there is provided a method of protein sequence analysis, the method including identifying, from among a first group of aligned protein sequences having at least a threshold degree of alignment with a first protein sequence, a second group of at least one of the aligned sequences having at least one insertion or deletion ("indel") relative to the first protein sequence satisfying a predefined condition.

The first protein sequence may include a protein sequence of a pathogen, and the predefined condition may be indicative of the potential presence of a drug target for the pathogen associated with the at least one indel.

At least one of the first group of aligned protein sequences may include a protein sequence of a host organism associated with the pathogen.

The predefined condition may include a minimum length of the at least one indel. The minimum length may include a minimum length of at least four contiguous amino acids.

Alternatively, or in addition, the predefined condition may include a maximum length of the at least one indel.

The maximum length may include a maximum length of 50 contiguous amino acids.

The predefined condition may include a predefined range of length of the at least one indel. The predefined range may include a range of four to 50 contiguous amino acids.

The method may further include comparing a plurality of protein sequences to the first protein sequence to identify the first group of aligned protein sequences having at least the threshold degree of alignment with the first protein sequence.

The threshold degree of alignment may be at least 70% alignment between each of the aligned protein sequences and the first protein sequence. More particularly, the threshold degree may be at least 80% alignment, or may be at least 90% alignment, for example.

The method may further include successively selecting each one of a plurality of protein sequences as the first protein sequence, and repeating the identifying for the each one of the plurality of protein sequences.

The method may further include storing the second group of aligned sequences in a storage medium.

In accordance with another aspect of the invention, there is provided an apparatus for protein sequence analysis. The apparatus includes at least one processor circuit configured to perform the methods disclosed herein.

In accordance with another aspect of the invention, there is provided a computer program including code means that when executed on at least one processor circuit carry out the methods disclosed herein.

In accordance with another aspect of the invention, there is provided a computer program on a carrier carrying code that when executed on at least one processor circuit directs the at least one processor circuit to carry out the methods disclosed herein.

In accordance with another aspect of the invention, there is provided a computer-readable medium providing code segments for directing at least one processor circuit to carry out the methods disclosed herein.

In accordance with another aspect of the invention, there is provided a signal embodied in a transmission median including code segments for directing at least one processor circuit to carry out the methods disclosed herein.

In accordance with another aspect of the invention, there is provided a signal embodied in a carrier wave including code segments for directing at least one processor circuit to carry out the the methods disclosed herein.

In accordance with another aspect of the invention, there is provided a method including generating a signal including code segments for directing at least one processor circuit to carry out the methods disclosed herein.

In accordance with another aspect of the invention, there is provided a method including propagating a signal including code segments for directing at least one processor circuit to carry out the methods disclosed herein.

In accordance with another aspect of the invention, there is provided an apparatus for protein sequence analysis, the apparatus including:
a) means for receiving data representing a first group of aligned protein sequences having at least a threshold degree of alignment with the first protein sequence; and
b) means for identifying, from among the first group, a second group of at least one of the aligned sequences having at least one insertion or deletion ("indel") relative to the first protein sequence satisfying a predefined condition.

In accordance with another aspect of the invention, there is provided a method of protein sequence analysis, the method including:
a) receiving identifications of aligned protein sequences at least some of which have at least a threshold degree of alignment with a pathogen protein sequence and have at least one insertion or deletion ("indel") relative to the pathogen protein sequence satisfying a predefined condition; and b) identifying drug target suitability characteristics of a region of the pathogen protein sequence in response to the group of aligned sequences.

Identifying the characteristics of the aligned sequences may include, for each of the aligned sequences, identifying characteristics of the at least one indel and a complementarity region thereof.

Identifying characteristics of the at least one indel and the complementarity region may include one or more of the following: identifying secondary structure of the pathogen protein sequence and the aligned protein sequences; identifying tertiary structure of the pathogen protein sequence and the aligned protein sequences; identifying quaternary structure of the pathogen protein sequence and the aligned protein sequences; and performing functional analysis of the pathogen protein.

The method may further include identifying a moiety capable of binding to a target region of the pathogen protein sequence.

In accordance with another aspect of the invention, there is provided a data structure embodied in a medium including respective fields for storing: an identification of a protein sequence; all identification of a pathogen protein sequence; alignment data indicative of alignment identity between the protein sequence and the pathogen protein sequence; and insertions or deletions ("indels") of the protein sequence relative to the pathogen protein sequence.

In accordance with another aspect of the invention, there is provided a data structure embodied in a medium for storing data produced by the methods disclosed herein, the data structure including respective fields for storing: an identification of the first protein sequence; an identification of one of the first group of aligned protein sequences; a degree of alignment identity between the one of the first group and the first protein sequence; and insertions or deletions of the one of the first group relative to the first protein sequence.

Embodiments of this invention may provide a method of identifying members of a group of homologous proteins, which members have a high probability of being effected by a drug or have a high probability of being bound to a specific binding moiety. In this specification, such homologous proteins are referred to as essential proteins. Members of a group of homologous proteins having or lacking an indel as defined herein may be identified or selected as targets. The indel or region lacking an indel may be used for design of a specific binding moiety as described herein. Embodiments of this invention may be particularly useful for identifying target homologous proteins from pathogenic organisms. Thus, such embodiments of this invention may involve indel comparison between species identified as either host or pathogenic.

Embodiments of this invention may also provide instructions, including instructions in machine-readable form, for operation of a computer implemented method for performing the aforementioned methods, including the specific embodiments of such methods described herein. Embodiments of this invention may also provide a machine readable medium containing such instructions. Embodiments of this invention may also provide a database in which information regarding indels is related or associated with information regarding homology of proteins in which the indels occur and which may also be related or associated with information concerning whether a source organism is a host or a pathogen. Embodiments of his invention may also provide methods for using such a database for identification or selection of drug targets in pathogenic organisms and for providing specific sequence information which may be used for drug development or design. In the latter situation, such drug design may be based on three-dimensional models prepared by computer implemented methods, which models are based on the sequence information referred to above. Further, embodiments of this invention may provide methods in which protein fragments including indels or regions of homologous proteins not containing an indel are used for screening compounds capable of binding to or affecting the activity of such protein fragments.

Embodiments of this invention build upon the discovery that essential pathogen proteins can contain insertions or deletions compared to their host homologues conferring structural differences that may be exploited as drug targets specific for the pathogen. Proteins that are essential to pathogen survival can contain discrete, heretofore unrecognized indels which differentiate them from their otherwise highly related mammalian homologues. Up to now, because of their high degree of relatedness and because they are essential for survival in both host and pathogen, these proteins have not been candidate drug targets.

The importance of identification of relative insertions and deletions (or indels) in protein sequences has been previously described (e.g. PCT application publication no. WO97/01578). However, there have been no comprehensive indel investigations taking into account available sequence information and information concerning homologous proteins. Embodiments of this invention may provide a comprehensive database and method of analysis based on frequency of insertions and deletions amongst otherwise highly homologous proteins. Importantly, this type of analysis can identify a large data set of drug targets in pathogenic microorganisms. Once identified the unexpected structural differences in otherwise homologous proteins may be exploited for targeted drug development.

Embodiments of this invention may permit the identification of pathogen proteins that are critical for fitness and survival and which also show insertions/deletions compared to their host homologues. A relative insertion or deletion in the sequence of an essential pathogen protein may confer to the region, a unique defined secondary structure, such as hairpin fold, and that such a structural feature may be exploited as potential site for selective drug binding. The information herein concerning EF-1α is illustrative of the potential of certain embodiments of this invention and is not intended to be limiting as to the scope of this invention.

EF-1α, or a close homologue, is expressed in all cells, whether they are eukaryotic or prokaryotic in origin. It serves as an essential enzyme for the translation of proteins from messenger RNA (mRNA) by controlling the speed and placement of tRNA-amino acid complexes in a growing polypeptide chain. Without EF-1α, protein synthesis ceases, as does cell viability.

We have now characterized a pathogenic form of EF-1α derived from protozoan sources and have found that the pathogenic form is a specific SHP-1 binding and activating protein. Protein modeling identifies important structural and functional differences between the pathogenic and mammalian forms of EF-1α, with such differences being shared amongst other trypanosomatids which cause trypanosomiases, and unrelated protozoa. Further, infection of macrophages with *leishmania* causes redistribution of host as well as pathogen EF-1α. The distinct properties of pathogen EF-1α in comparison to the human protein and the essential role for EF-1α in protein translation and other cell functions, makes EF-1α a drug target for treatment of protozoan related diseases.

Molecular modeling of EF-1α illustrates a species differentiated 12 amino acid 'indel' (insertion/deletion sequence) that forms a surface exposed hairpin loop on human EF-1α, which is conversely deleted in the protozoan protein. Thus, there is a significant region of differentially exposed amino acids between protozoan and human EF-1α proteins, two proteins that are otherwise highly conserved. Based upon the results herein, and the known phylogeny of protozoan or protozoan like organisms, there are numerous pathogens that lack the aforementioned indel in EF-1α, including: *leishmania* (agent of leishmaniasis), *Trypanoyoma brucei* and *Trypanosoma cruzi* (respectively agents of sleeping sickness and Chagas disease), cryptosporidium (agent of cryptosporidiosis), entamoeba. (agent of amebiasis), *Giardia* (agent of giardcasis), *plasmodium* (agent of malaria), *Toxoplasma gondi* (an agent of *toxoplasma*) and *Pneumocystitls carinis* (an agent of pneumocystitus). EF-1α is multifunctional and plays at least two essential roles, these being the regulation of protein synthesis and as a virulence factor. A virulence factor renders a host cell permissive for infection and may possess one or more of the following: a component of a pathogen that when deleted specifically impairs virulence but not viability; a microbial product that permits a pathogen to cause disease; a component of a pathogen that damages the host; or an effector molecule that 1) produces changes in target cells outside of the organism itself, 2) is found only in pathogenic species or variety of the organism, and 3) is located on the surface of the organism or is secreted by the organism.

An example of homologous, essential proteins are the EF-1α proteins from any of the sources described herein. Preferably, such homologous proteins as referred to herein generally will have at least 70% sequence identity as determined by suitable algorithms, including BLAST using default parameters. Preferably, sequence identity between homologous proteins will be high, with approximate percentage identity from least to most preferable being: 70, 75, 80, 85, 90 and greater than 90%.

The additional 12 amino acids found within human EF-1α form a hairpin-loop structure and is an indel. This indel is located on the exterior of the protein and is closely opposed to the main body of EF-1α. The "unshielded" region of the pathogen EF-1α protein, which is concealed or shielded by the indel in the human protein (henceforth referred to as an "indel complementarity region"), contains several highly polar residues with exposed side chains. Therapeutic compounds can bind specifically to this indel complementarity region on pathogen EF-1α and disrupt its function, without interfering with the corresponding region in the host homologue that is concealed by the indel. In addition, compounds that bind to pathogen EF-1α, but not to the human homologue can be used for effective diagnostic tests. Such binding compounds include antibodies, peptides, proteins and small molecule compounds.

Embodiments of this invention may include methods for identifying, detecting, or assaying pathogenic proteins which include determining whether a protein member of a homologous group of proteins includes an indel as described herein. These methods may be performed, for example, by sequencing (actual or predicted) and comparison of such sequence to homologous proteins, particularly those from pathogenic and host organisms.

Embodiments of this invention may include methods for identifying, detecting, or assaying moieties for specific binding to pathogenic proteins or an ability to modulate the activity of a pathogenic moiety, which methods include determining whether a putative specific binding moiety binds to a pathogenic protein as described herein and not to a host protein (or binds to the pathogenic protein to a greater extent than the host form); or, utilizing a first three-dimensional model of a pathogenic indel or indel complementarity region and a second three-dimensional model of a putative specific binding moiety, positioning both the three-dimensional models to form a third three-dimensional model of a specific binding complex and determining whether the binding complex is favourable (for example, without unacceptable hindrances such as steric, electrostatic, and hydrophobic hindrances). The latter methods may also be used for designing a specific binding moiety for pathogenic protein wherein a three-dimensional model of a putative specific binding moiety is altered to optimize binding between the moiety and the indel or indel complementarity region. Using the example herein, an indel complementarity region may include regions of contiguous amino acids from the following regions of *leishmania* EF-1α or from corresponding (homologous) regions of another pathogenic EF-1α:
1. amino acids 215-224 TLLDALDMLE (SEQ ID NO: 1)
2. amino acids 186-194 EKVRFIPIS (SEQ ID NO: 2)
3. amino acids 158-168 KTVTYAQSRYD. (SEQ ID NO: 3)

In the case of the example, the specific binding moiety may be capable of binding with, or such binding may be optimized to occur with one or more contact residues such as any of the following amino acids from *leishmania* EF-1α or a similarly placed charged or polar amino acid from another pathogenic EF-1α:

Glutamate (E) 186
Lysine (K) 187
Arginine (R) 189
Aspartate (D) 218
Aspartate (D) 221
Methionine (M) 222
Glutamate (E) 224

The aforementioned methods may additionally include one or more of: synthesizing a specific binding moiety, and combining a specific binding moiety with a pathogenic protein. These methods may further include methods of detecting, identifying, or assaying binding to the protein, as described above.

Embodiments of this invention may also include moieties capable of specific binding to pathogenic proteins identified, detected, synthesized, designed or assayed by the methods of this invention. By "specific binding" it is meant that the moiety is capable of preferentially binding to a pathogenic protein as described herein as compared to host proteins. Preferably, such a moiety will exhibit substantially no binding to the host form. Such binding moieties may be employed in assays for the protein and as specific targeting ligands (e.g. for labeling or directing a further moiety to the location of the pathogenic protein). In some embodiments, such moieties may modulate the activity of the protein. Preferably, the latter moieties will modulate the activity of pathogenic proteins in terms of essential function or function as a pathogen virulence factor. Specific binding moieties of embodiments of this invention may be chemical moieties designed to bind with contact residues in an indel or indel complementarity region as defined herein. Such moieties may be peptides or non-peptide molecules. Such moieties may be antibodies or antibody fragments capable of binding to an antigenic determinant of an indel or indel complementarity region. In addition, specific binding moieties of embodiments of this invention may shield the indel complementarity region without directly binding to the region. Specific binding moieties of embodiments of this invention may include therapeutic moieties for treatment of infections by organisms possessing pathogenic proteins. Accordingly, embodiments of this invention may include the use of such therapeutic moieties in treatment and may provide pharmaceutical compositions and formulations including specific binding moieties of embodiments of this invention together with one or more acceptable pharmaceutical carriers.

Embodiments of this invention may also include a method for modulating the activity of a pathogenic protein described herein including contacting a pathogenic protein with a specific binding moiety of an embodiment of this invention capable of modulating a function of the protein. Preferably, the modulation includes antagonism of a pathogenic function.

BRIEF DESCRIPTION OF THE DRAWINGS

FIG. 1 is a block diagram of a system for protein sequence analysis according to a first embodiment of the invention.

FIG. 2 is a flow chart of a protein sequence analysis routine executed by a processor circuit of the system shown in FIG. 1.

FIG. 3 is a block diagram of a system for protein sequence analysis according to a second embodiment of the invention.

FIG. 4 is a flow chart of a protein partition routine executed by at least one processor circuit of the system shown in FIG. 3.

FIG. 5 is a flow chart of a BLAST analysis execution routine executed by at least one processor circuit of the system shown in FIG. 3.

FIG. 6 is a flow chart of a BLAST analysis distribution routine executed by at least one processor circuit of the system shown in FIG. 3.

FIG. 7 is a flow chart of a significant indel identification routine executed by at least one processor circuit of the system shown in FIG. 3.

FIG. 8 is a flow chart of a significant indel analysis distribution routine executed by at least one processor circuit of the system shown in FIG. 3.

FIG. 9 is an illustrative example of a data structure produced by the system shown in FIG. 3. (Query amino acid sequence (SEQ ID NO: 5); Consensus amino acid sequence (SEQ ID NO: 6); and Subject ("sb;ct") amino acid sequence (SEQ ID NO: 7)).

DETAILED DESCRIPTION

Definitions

In this specification, the term "amino acid" means any of the organic compounds that contain one or more basic amino groups and one or more acidic carboxyl groups and that are polymerized to form peptides and proteins; only 20 of the more than 80 amino acids found in nature serve as building blocks for proteins.

In this specification, the term "protein sequence" means a representation of the amino acid constituents that make up a protein or peptide. A protein sequence is usually represented by a linear sequence of the standard single letter codes for the constituent amino acids.

In this specification, the term "essential" with reference to a protein, refers to the product of a gene where a mutation in the gene or the absence of the gene product or the absence of function of the gene product is detrimental to the pathogen. Whereby, detrimental to the pathogen means that such a mutation in the gene or the absence of the gene product or the absence of function of the gene product will result in death of the pathogen, lack of pathogen viability, lack of pathogenicity of the pathogen, and/or inability of the pathogen to reproduce in the host organism.

In this specification, the term "indel" refers to a region of amino acid sequence that includes all insertions and deletions in at least one amino acid sequence when aligned with another amino acid sequence, where the two sequences share overall similar sequences of amino acids. Where two sequences have overall similar sequences, that means that the two sequences when aligned contain primarily identical or conserved amino acids at corresponding amino acid positions. Typically, such an indel will have a maximum number of amino acids the same as or less than the following: 50, 40, 30, 25, 20 and 15. Also the number of amino acids in an indel needed to be considered significant is any number greater than three.

In this specification, the term "pathogen" means any organism (usually a microorganism) which by direct interaction with (infection of) a second organism (by convention a multicellular organism) causes disease in the second organism. The definition as used herein is also meant to include parasites and toxinogenic organisms.

In this specification, the term "host" means any organism on or in which a pathogen or parasite or toxinogenic organism is able to live or reproduce.

In this specification, the term "identity" means that all the amino acids at a single position are identical when two or more amino acid or protein sequences are aligned.

Methods

A) Protein Sequence Analysis Method—Indel Identification

To perform a comprehensive indel analysis, sequences may be collected for analysis from numerous databases, as represented by the following examples:

SWISS-PROT a protein sequence database that also provides a high level of annotations relating to the function of a protein, its domains structure, post-translational modifications, variants, etc. (Bairoch A. and Apweiler R. (2000) Nucleic Acids Res. 28(1):45-48; Bairoch A. and Apweiler R. (1997) J. Mol. Med. 75(5):312-316; Junker V. L. et al. (1999) Bioinformatics 15(12):1066-1007);

TrEMBL a computer-annotated supplement of SWISS-PROT that contains all the translations of EMBL nucleotide sequence entries (Bairoch A. and Apweiler R. (2000) Nucleic Acids Res. 28(1):45-48); and nr database compares all non-redundant GenBank CDS translations plus protein sequences from other databases such as PDB, SwissProt, PIR and PRF.

Alignments of protein sequences may be conducted using existing algorithms to search databases for sequences similar to a query sequence. Protein sequence alignments are not generally limited by protein type or organism.

One alignment method is the Smith-Waterman algorithm (Smith, T. F. and Waterman, M. S. 1981. Journal of Molecular Biology 147(1):195-197), which uses dynamic programming to determine how an optimal alignment between the query sequence and a database sequence can be produced. This alignment is obtained by determining what transformations the query sequence would need to undergo to match the database sequence. Transformations include substituting one character for another and inserting or deleting a string of characters. A score is assigned for each character-to-character comparison-positive scores for exact matches and some substitutions, negative scores for other substitutions and insertions/deletions. The first character in an insertion or deletion gap is scored with a gap open penalty and subsequent characters are scored with a gap extension penalty. Scores are obtained from statistically-derived scoring matrices. The combination of transformations that results in the highest score is used to generate an alignment between the query sequence and database sequence.

The Needleman-Wunsch (Needleman, S. B. and Wunsch, C. D. 1970. Journal of Molecular Biology 48(3):443-453) algorithm is similar to the Smith-Waterman algorithm, but sequence comparisons are global, not local. Global comparisons force an alignment of the entire query sequence against the entire database sequence. While local alignments always begin and end with a match, global alignments may begin or end with an insertion or deletion (indel). For a given query sequence and database sequence, a global score will be less than or equal to a local score due to indels on the ends.

As an alternative to the above algorithms, a Hidden Markov Model (HMM) search (Eddy, S. R. 1996. Current Opinion in Structural Biology 6(3):361-365) could be used to generate protein sequence alignments. HMM scoring weighs the probability of a match being followed by insertions/deletions or vice-versa. In addition, HMMs allow insertion to deletion transitions (and vice versa) and scoring of begin and end states to control whether a search is run globally or locally.

One or more of the above algorithms may be used in an alignment program to generate protein sequence alignments. A person killed in the art has numerous sequence alignment programs to choose from, that incorporate a variety of different algorithms. One example of an alignment program is BLASTP (Altschul, S. F., et al. (1997) Nucleic Acids Res. 25(17):3389-3402). Other alignment programs are CLUSTAL W and PILEUP. The standard output from a BLASTP run contains enough information to conduct further indel analysis as described below.

The alignment results are collected in an output file where each individual sequence is identified by protein, organism, family, genus, superkingdom and characterized by whether the organism is parasitic or free living, pathogenic or non-pathogenic etc.

The alignment results that are collected are then analyzed (parsed) to identify potentially significant indels. From the initial alignment results, alignments are identified which share at least 70% identity and preferably greater than 70% identity. Only those that have at least 70% identity are further selected from.

When aligned, the sequences produce gaps, which are predicted indels. These predicted indels may then be characterized on the basis of their size (e.g. four or more amino acids). The sequence identity and indel size information associated with each sequence alignment is then stored for subsequent retrieval and analysis.

Exemplary System

Referring to FIG. 1, an exemplary apparatus for protein sequence analysis according to a first embodiment of the invention is shown generally at 20. In this embodiment, the apparatus includes a processor circuit 21, which is configured to identify, from among a first group of aligned protein sequences having at least a threshold degree of alignment with a first protein sequence, a second group of at least one of said aligned sequences having at least one insertion or deletion ("indel") relative to said first protein sequence satisfying a predefined condition.

In this embodiment, the processor circuit 21 includes a microprocessor, which may be housed in a general purpose or special purpose computer (not shown), for example. More generally, however, in this specification, the term "processor circuit" is intended to broadly encompass any type of device or combination of devices capable of performing the functions described herein, including (without limitation) other types of microprocessors, microcontrollers, other integrated circuits, other types of circuits or combinations of circuits, logic gates or gate arrays, or programmable devices of any sort, for example, either alone or in combination with other such devices located at the same location or remotely from each other, for example. Additional types of processor circuits will be apparent to those ordinarily skilled in the art upon review of this specification, and substitution of any such other types of processor circuits is considered not to depart from the scope of the present invention as defined by the claims appended hereto.

In this embodiment, the processor circuit 21 is in communication with a random access memory (RAM) 22, which may be either separate from or integral with the processor circuit, or which may include a combination of on-board and external RAM. The processor circuit 21 is also in communication with a storage medium 23, which in this embodiment includes a hard disk drive, although alternatively, other types of storage media may be substituted. In this embodiment, the storage medium 23 acts as a computer-readable medium storing various codes for directing the processor circuit 21 to carry out the functions disclosed herein, including an analysis routine 24. Alternatively, however, such codes may be provided by other computer-readable media. For example, fixed media such as a compact disc or floppy diskette, or a transmission medium such as a communications network, may provide such codes. Generally, any medium capable of providing signals for directing the processor circuit 21 to perform the functions disclosed herein may be substituted if desired. In this embodiment, the storage medium 23 also includes a results store 25, for storing data structures including results of the execution of the analysis routine 24 by the processor circuit 21.

In this embodiment, the processor circuit 21 is also in communication with a sequence database 26, which may include may include any one or more of the SWISS-PROT, TrEMBL or nr databases referred to above, or any other suitable sequence database. The processor circuit 21 may be in direct communication with the database, or may be in indirect communication therewith, for example, via a network (not shown). If desired, the storage medium 23 may store the desired sequences and may thus act as the sequence database 26.

In this embodiment, the processor circuit 21 is also in communication with a user interface 27, which may include a keyboard and a display, for example.

Figure 2:
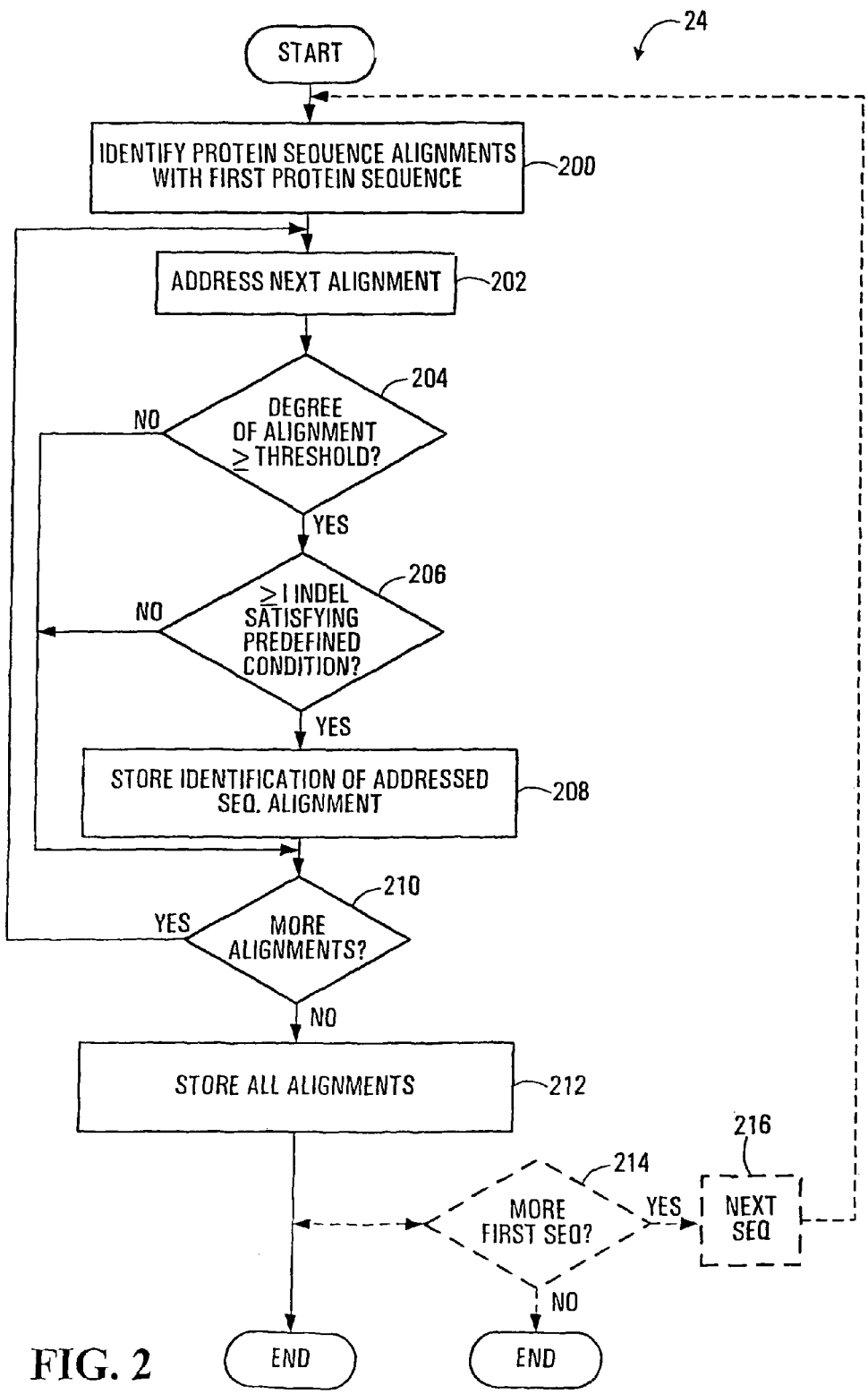

Referring to FIGS. 1 and 2, the analysis routine is shown generally at 24 in FIG. 2. Generally, the analysis routine 24 configures the processor circuit 21 to identify, from among a first group of aligned protein sequences having at least a threshold degree of alignment with a first protein sequence, a second group of at least one of said aligned sequences having at least one insertion or deletion ("indel") relative to said first protein sequence satisfying a predefined condition. More particularly, in this embodiment the first protein sequence includes a protein sequence of a pathogen, although alternatively, other types of protein sequences may be substituted if desired. The identification of the first protein sequence may be supplied by a user (not shown) of the apparatus 20 at the time the analysis routine 2 is first executed. For example, the user may use the user interface 27 to either manually enter the first protein sequence or to enter a location or filename accessible by the processor circuit in which the first protein sequence is stored. The processor circuit 21 may store the first protein sequence in either the RAM 22 or the storage medium 23 or both, for use in execution of the analysis routine.

The analysis routine 24 includes a first block 200 of codes, which directs the processor circuit 21 to identify a first group of aligned protein sequences, or in other words, protein sequences having a substantial alignment identity with the first protein sequence. To achieve this, block 200 directs the processor circuit 21 to execute the BLASTP routine referred to earlier herein, to identify aligned protein sequences stored in the database 26, i.e., protein sequences that are aligned with the first protein sequence. Block 200 directs the processor circuit to store the output results of the BLASTP routine in an alignment results store 201 of the results store 25 of the storage medium 23. Alternatively, however, any other suitable alignment routine may be substituted for the BLASTP routine executed at block 200.

Block 202 then directs the processor circuit 21 to address the next successive aligned protein sequence stored in the alignment results store 201 in the storage medium 23, commencing with the first such aligned sequence when block 202 is first executed.

Block 204 then directs the processor circuit 21 to determine whether the degree of alignment, or in other words the alignment identity, between the currently addressed aligned protein sequence and the first protein sequence, is at least equal to a threshold degree of alignment. In this embodiment, the threshold degree of alignment is 70%. Alternatively, however, depending upon the application, other threshold degrees of alignment may be substituted. For example, minimum threshold degrees of alignment identity of 75%, 80%, 85%, or 90% may be preferred, depending upon the nature and scope of the particular application. Preferably, the threshold degree of alignment is an adjustable parameter of the analysis routine 24, that the user may adjust prior to execution of the analysis routine by entering the desired threshold using the user interface 27, for example. If the alignment identity between the currently addressed protein sequence alignment and the first protein sequence is less than the threshold degree, then the currently addressed protein sequence is effectively discarded as irrelevant, and the processor circuit is directed to block 210 below to determine whether any further aligned sequences remain to be analyzed.

If at block 204 the alignment identity between the currently addressed aligned protein sequence and the first protein sequence is determined to be greater than or equal to the threshold degree of identity, block 206 directs the processor circuit 21 to determine whether the currently addressed aligned protein sequence has at least one indel relative to the first protein sequence satisfying a predefined condition. In this embodiment, the predefined condition includes a minimum length of the indel. More particularly, in this embodiment the minimum length of the indel is at least four contiguous amino acids. In this embodiment, the predefined condition also includes a maximum length of the indel. More particularly, in this embodiment the maximum length is 50 contiguous amino acids. Effectively, therefore, in this embodiment the predefined condition includes a range of length of the at least one indel, which in this embodiment is a range of four to 50 contiguous amino acids. Alternatively, however, other types of predefined conditions may be substituted, depending upon the nature and scope of the particular application. Preferably, the predefined condition is an adjustable parameter of the analysis routine 24, that the user may adjust prior to execution of the analysis routine by entering the desired threshold using the user interface 27, for example. If the currently addressed aligned protein sequence does not have at least one indel satisfying the predefined condition, then the currently addressed protein sequence is effectively discarded as irrelevant, and the processor circuit is directed to block 210 below to determine whether any further aligned protein sequences remain to be analyzed.

If at block 206 it is determined that the currently addressed aligned protein sequence does have at least one indel satisfying the predefined condition, block 208 directs the processor circuit 21 to store an identification of the currently addressed aligned protein sequence. In this embodiment the processor circuit is directed to store the addressed sequence in an alignments store 209 of the results area 25 of the storage medium 23, although alternatively, the aligned protein sequence may be stored elsewhere, such as the RAM 22, for example.

Block 210 then directs the processor circuit 21 to determine whether all of the aligned protein sequence results produced at block 200 have been addressed at blocks 202 to 208 above, and if not, the processor circuit is directed back to block 202 to address the next aligned protein sequence in the alignment results store 201 and to proceed to execute blocks 204, 206 and 208 as described above. It will be appreciated that the successive execution of block 204 on each of the aligned protein sequences produced at block 200 effectively directs the processor circuit to compare a plurality of protein sequences to the first protein sequence to identify the first group of aligned protein sequences having at least the threshold degree of alignment with the first protein sequence. Alternatively, this comparison, including the use of the threshold, may be combined into block 200 as discussed above, if desired.

If no more aligned sequences remain to be addressed, block 212 directs the processor circuit 21 to store the significant indels, i.e., the second group of aligned sequences identified at block 206, in the storage medium 23. To achieve this, in the present embodiment block 212 directs the processor circuit to store the contents of the significant indels store 209 in a data structure within a text file in the storage medium 23. Alternatively, other storage methods or formats may be substituted. The analysis routine 24 is then ended.

If desired, the analysis routine 24 may be repeatedly executed to identify potentially significant indels for a number of different pathogens or other specified first protein sequences. In other words, the processor circuit 21 may be configured to successively select each one of a plurality of protein sequences as the first protein sequence, and may be configured to repeat the identifying steps discussed above at blocks 204 and 206 for each one of the plurality of protein sequences. To achieve this, the analysis routine 24 may include additional block of codes 214 and 216 shown in broken outline in FIG. 2. Block 214 directs the processor circuit 21 to determine whether any further pathogens or other first protein sequences have been specified by the user for analysis, and if so, block 216 directs the processor circuit to address the next such first protein sequence, and to return to block 200 to commence re-execution of the analysis routine 24 as discussed above.

Distributed Processing System

Depending upon the scope of the required analysis and upon available processing power, the analysis of large numbers of proteins may be very time consuming and may require significant computing resources if executed entirely on a single processor circuit. As some applications of specific embodiments of the invention may entail analysis of large groups of protein sequences (for example, some databases include 800,000 or more relevant protein sequences), the concurrent or parallel use of a plurality of processor circuits may facilitate and expedite such analysis. Where a plurality of processor circuits are being used to analyze a subset of proteins it is possible to minimize data loss and time loss, because a fatal error in a routine being executed on any one of the processor circuits handling an analysis job on a subset of proteins is likely to result in a smaller loss of data and time.

Figure 3:
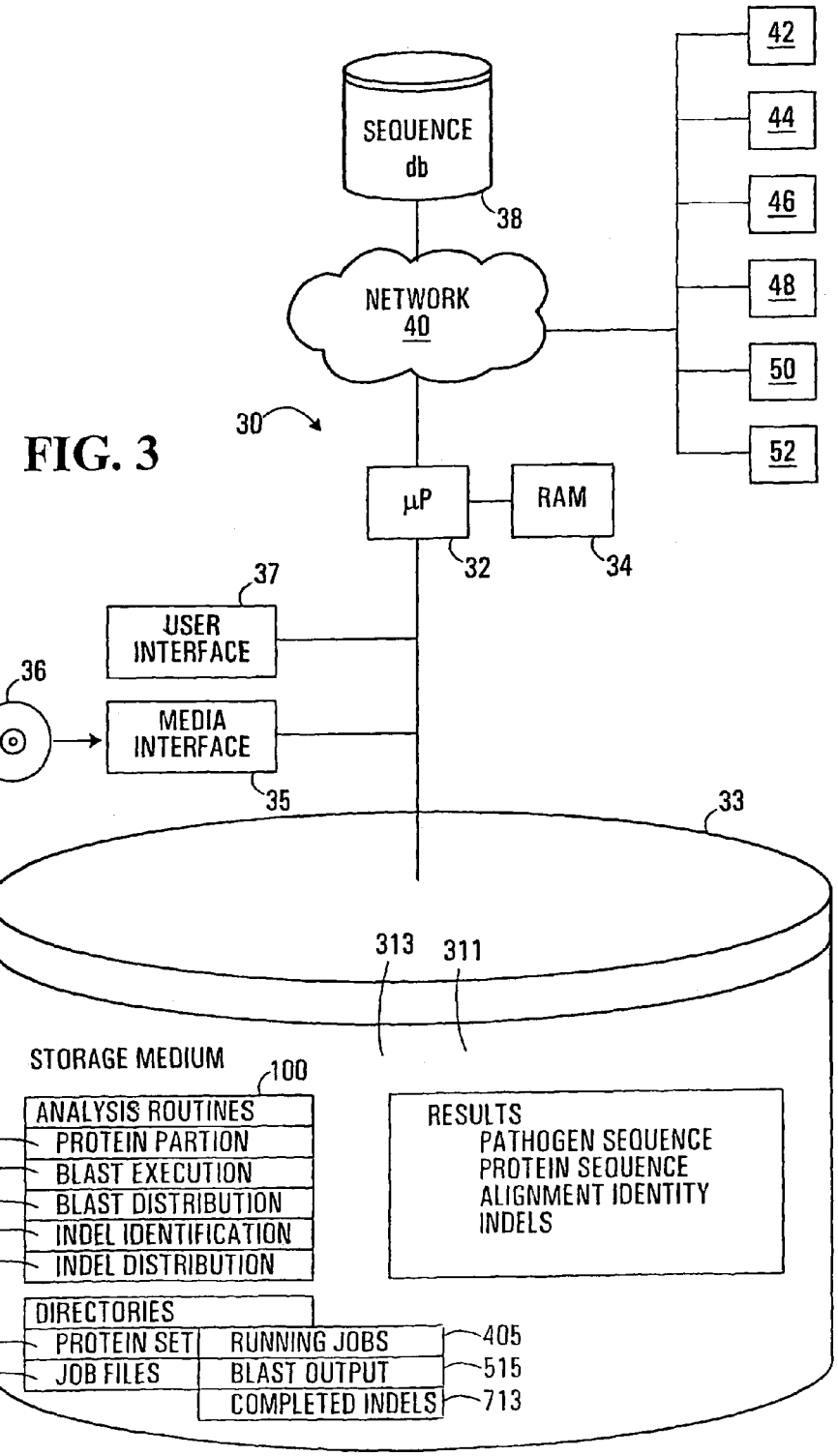

Accordingly, referring to FIG. 3, an apparatus for protein sequence analysis according to a second embodiment of the invention is shown generally at 30. In this embodiment, the apparatus includes a processor circuit 32 in communication with a storage medium 33, a random access memory (RAM) 34, a media interface 35, and a user interface 37.

In the present embodiment, the processor circuit 32 includes a microprocessor. Alternatively, however, other types of processor circuits may be substituted, such as those noted above in connection with the previous embodiment, for example.

Generally, the media interface 35 is used to read data signals from a computer-readable medium 36. More particularly, in this embodiment the media interface 35 includes a CD-RW drive for reading signals from the medium 36, which in this embodiment is a compact disc. Alternatively, any other suitable types of media interfaces and media may be substituted. In his embodiment, the user interface 37 includes a keyboard and a display device (neither of which is shown in FIG. 3).

In this embodiment, the processor circuit 32 is in communication with a network 40, which in this embodiment includes a local area network in communication with the Internet. The processor circuit 32 is in communication, via the network 40, with additional processor circuits such as those shown at 42, 44, 46, 48, 50 and 52, for example. In this embodiment, each of the processor circuits 32, 42, 44, 46, 48, 50 and 52 is in communication via the network 40 with a sequence database 38, which may include any one or more of the SWISS-PROT, TrEMBL or nr databases referred to above, or any other suitable sequence database.

In this embodiment the storage medium 33 includes a hard disk drive, although other types of storage media may be substituted if desired. In the present embodiment, the storage medium 33 acts as a computer-readable medium storing codes for directing one or more of the processor circuits shown in FIG. 3 to perform the various functions disclosed herein. More particularly, in this embodiment the storage medium 33 stores a plurality of analysis routines 100, including a protein partition routine 300, a BLAST execution routine 400, a BLAST distribution routine 500, an indel identification routine 600, and an indel distribution routine 700. Alternatively, such routines may be stored on other computer-readable media, such as the medium 36, for example. In addition, in this embodiment the network 40 acts as a transmission medium providing codes for directing the processor circuits 42 to 52 to perform the various functions discussed below. More generally, any alternative way of generating data signals for directing the various processor circuits to perform the functions disclosed herein may be substituted.

Figure 4:
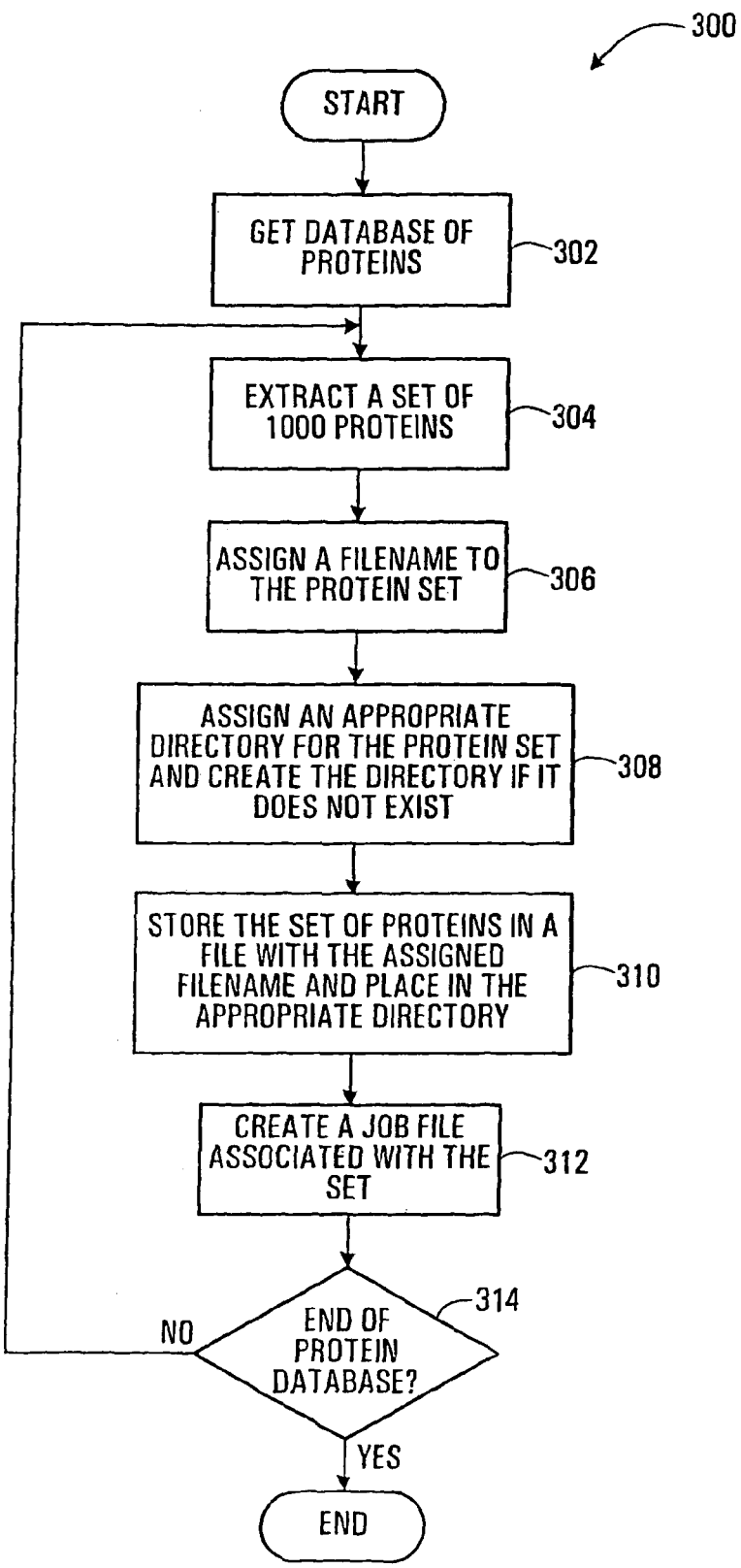

Referring to FIGS. 3 and 4, the protein partition routine is shown generally at 300 in FIG. 4. The protein partition routine 300 begins with a first block of codes 302 that directs the processor circuit 32 to access the sequence database 38.

Block 304 then directs the processor circuit 32 to extract a set of 1000 proteins and block 306 directs the processor circuit 32 to assign a name to the protein set according to the order that the protein set was extracted from the protein database (i.e. the fifth set would be "protein_set_5k.txt").

Block 308 directs the processor circuit 32 to assign a directory to the protein set (or to create one if one does not exist) In this embodiment, each directory includes 100 sets of proteins, each set including 1000 individual proteins. For example, the first directory is "/protein_sets/prot_set_100k/").

Block 310 directs the processor circuit 32 to store each set of proteins in a file with an assigned filename and place the file in a protein set directory in the storage medium 33. Block 312 then directs the processor circuit 32 to create a job file associated with the set (for example, set 5 would be assigned to job file "job_5k.txt"). Such job files are effectively used for communicating tasks to the various distributed processor circuits, as discussed in greater detail below. Block 312 directs the processor circuit 32 to store the job file in a job file directory 313 in the storage medium 33.

Finally, block 314 directs the processor circuit 32 to return to block 302 to select another set of proteins from the protein database and assign a filename, directory and job file to the selected set as described above until no more sets are found in the protein database.

Figure 5:
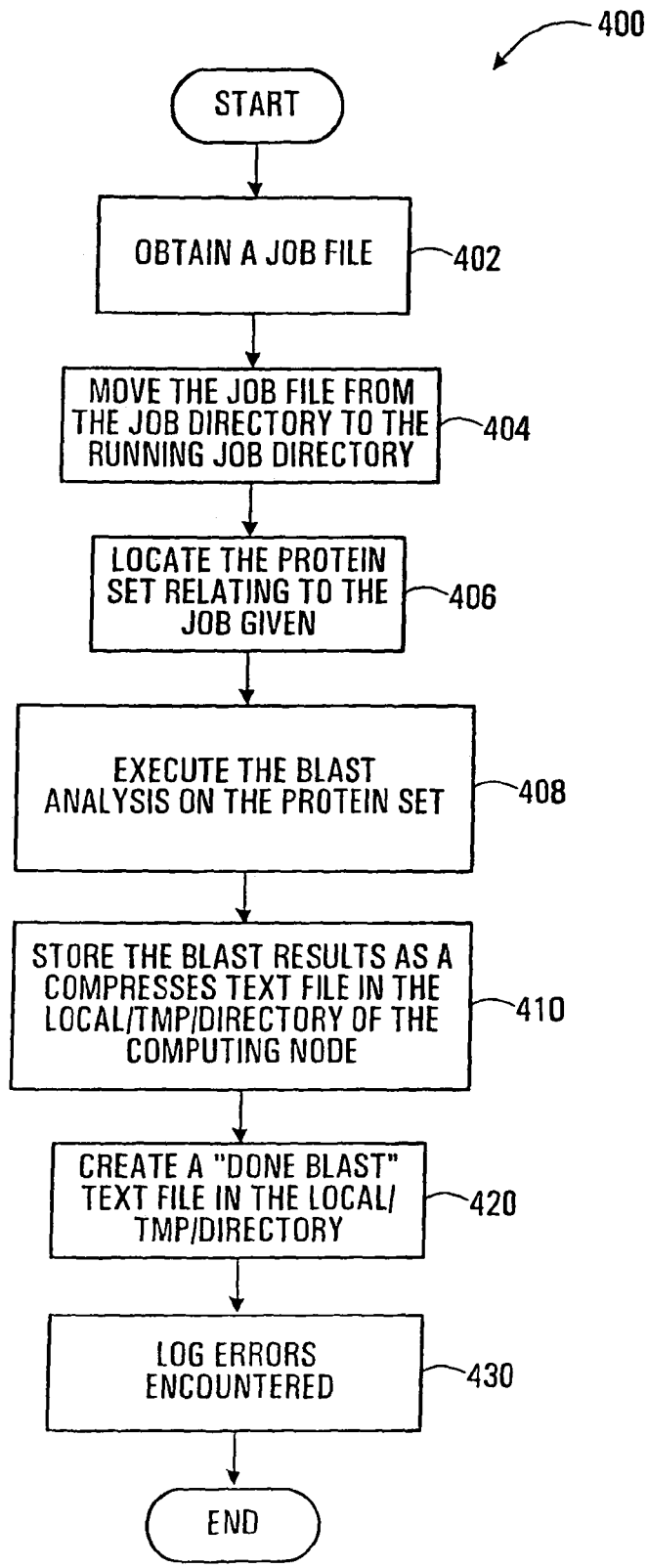

Referring to FIGS. 3 and 5, the BLAST analysis execution routine is shown generally at 400 in FIG. 5. Generally, in His embodiment, the BLAST analysis execution routine 400 directs the processor circuit to obtain a job file created under the direction of the protein partition routine 300 and to execute an alignment algorithm, which in this embodiment is a BLAST analysis, on the contents of the job file. Such job files are effectively distributed under the direction of the BLAST analysis distribution routine 500, discussed below. Thus, in view of the latter distribution of job files, the BLAST analysis execution routine 400 may be executed on any one of the processor circuits 32, 42, 44, 46, 48, 50 or 52 shown in FIG. 3. For ease of understanding, therefore, the present routine is described as being executed by the "processor circuit", with the understanding that any one of the distributed processor circuits may execute his routine.

The BLAST analysis execution routine 400 begins with a first block of codes 402, witch directs the processor circuit to obtain a job file (created by the processor circuit 32 under the direction of the protein partition routine 300, as discussed above) from the storage medium 33.

Block 404 then directs the processor circuit to move the job file from the job file directory 313 to a running job directory 405. This ensures that any fatal crashes by the processor circuit running the BLAST analysis execution routine 400 can easily be identified and allows for reanalysis if the BLAST analysis was not complete. Block 404 also directs the processor circuit to store all identification of itself in association with the file stored in the ruling job directory, to allow the processor circuit 32 to identify the processor circuit executing the particular job identified by the job file stored in the running job directory.

Block 406 directs the processor circuit to locate the protein set in the protein set directory 311 relating to the job file being analyzed.

Block 408 then directs the processor circuit to execute an alignment algorithm, which in this embodiment is a BLAST analysis routine as described above, on the protein set. Alternatively, other suitable alignment algorithms or methods may be substituted. It will be recalled that the protein set of the job file in the present embodiment includes 1000 protein sequences. Accordingly, in this embodiment, the alignment algorithm is effectively executed 1000 times in succession, each execution employing a different respective one of the 1000 protein sequences as the query sequence. With each such execution corresponding to each such selected query sequence, the processor circuit is directed to search the sequence database 38 for aligned protein sequences, i.e., protein sequences having a substantial alignment identity with the query sequence. The processor circuit is directed to store each such located set of aligned protein sequences in association with an identification of the query sequence that was used to locate the aligned sequences, as a query set. The processor circuit is directed to continue selecting successive aligned protein sequences of the protein set as the next query sequence, to repeat such searching of the database for sequences aligned with the query sequence, and to continue repeating such searching for each successive query sequence until all of the 1000 sequences of the protein set of the job file have been used as query sequences.

Block 410 then directs the processor circuit to store the completed BLAST results as a compressed text file (using gzip) to save disk space in a "local/tmp/directory" of a local storage medium accessible by the processor circuit. It will be appreciated that this BLAST results file effectively includes 1000 respective query sets representing the results of 1000 successive alignment searches for sequences aligning with 1000 respective query sequences.

Block 420 then directs the processor circuit to create a "done_blast" or BLAST output text file in the local/tmp/directory to effectively notify the processor circuit 32 that the BLAST analysis is complete (as discussed below in connection with the BLAST distribution routine 500, block 510 of the latter routine directs the processor circuit to periodically monitor the contents of the local/tmp/directory areas of the distributed processor circuits, to determine whether each such processor circuit has completed a BLAST analysis job). Block 430 then directs the processor circuit to log any errors that were encountered when running the BLAST analysis execution routine 400, in a local error log (not shown).

Figure 6:
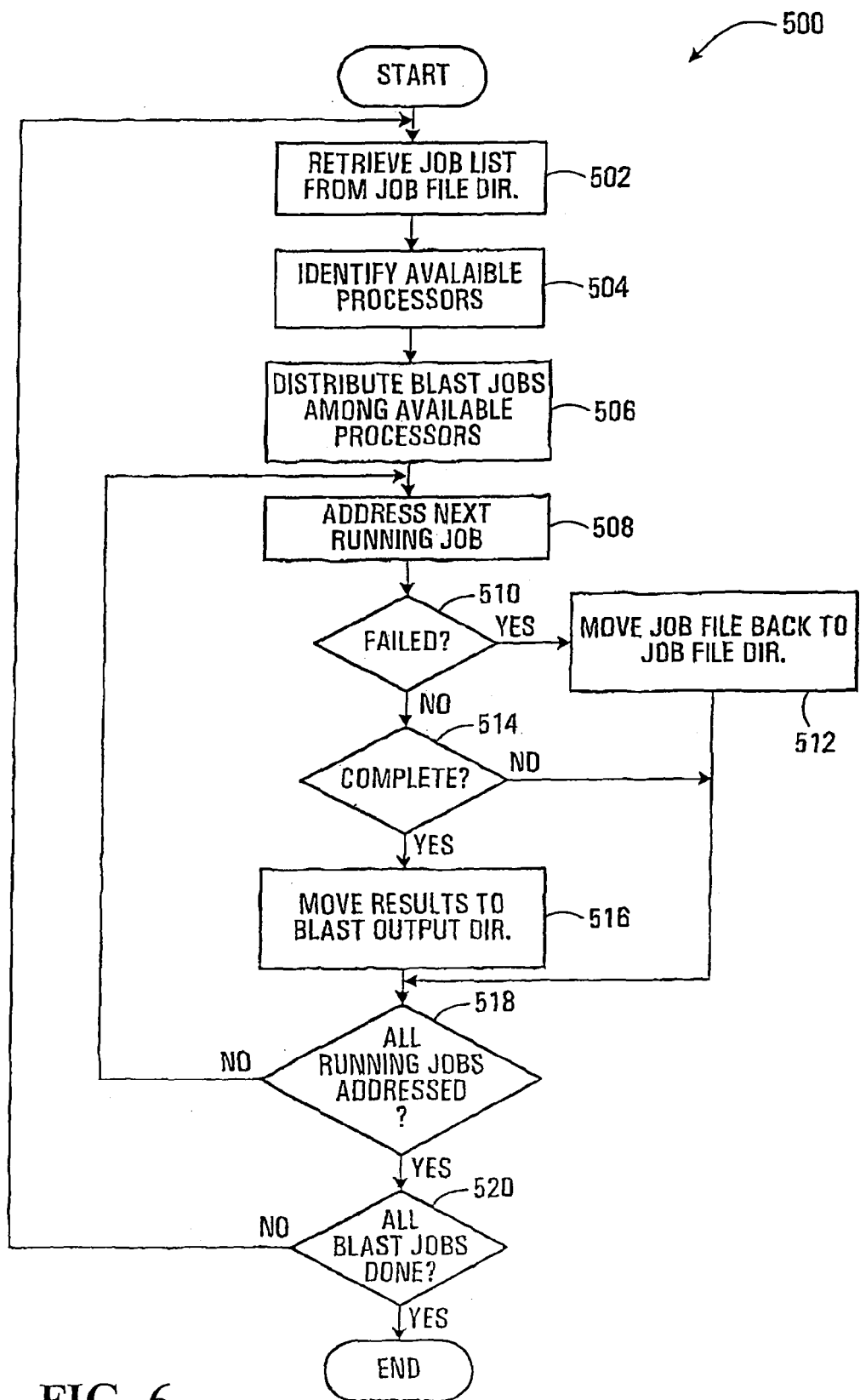

Referring to FIGS. 3 and 6, the BLAST analysis distribution routine is shown generally at 500 in FIG. 6. Generally, the BLAST analysis distribution routine 500 configures the processor circuit 32 to assign jobs to the various other processor circuits, each of which may execute a BLAST analysis execution routine 400 as described above.

In this embodiment, the BLAST analysis distribution routine 500 begins with a first block of codes 502 that directs the processor circuit 32 to retrieve a list of job files from the job files directory 313 in the storage medium 33.

Block 504 then directs the processor circuit 32 to determine which of the various distributed processor circuits shown in FIG. 3 are available for execution of BLAST analysis. This may be achieved by directing the processor circuit to communicate directly with the various distributed processor circuits, or alternatively, by communicating with a central network node, for example. In this embodiment, a processor circuit is considered to be available for BLAST analysis if it has a MIPS≧2000/equal to or better than a dual 1 GHz CPU and load averages of less than 2, although alternatively, other availability criteria may be substituted.

Block 506 then directs the processor circuit 32 to distribute one BLAST job to each of the available processor circuits. In this embodiment, the processor circuit 32 signals each such available processor circuit to execute the BLAST analysis execution routine 400, to obtain and analyze a job file as described above. Alternatively, any other suitable way of distributing tasks may be substituted.

Blocks 508 to 518 effectively direct the processor circuit 32 to monitor all BLAST jobs running on the available processor circuits. Block 508 directs the processor circuit to address the next running job identified in the running jobs directory 405 shown in FIG. 3, commencing with the first such running job when block 508 is first executed.

Block 510 directs the processor circuit 32 to determine whether the currently addressed running job has failed. This may be achieved, for example, by directing the processor circuit 32 to examine the contents of the local error log of the processor circuit in question (identified by the contents of the addressed running job directory record), to determine whether the error log includes an indication of a fatal error (as discussed above in connection with block 430 of the BLAST execution routine). This may also be achieved by determining whether a timeout has occurred, i.e., whether the processor circuit has been executing the running job for a longer period of time than expected without having completed it. Alternatively, other ways of detecting job failure may be substituted.

If at block 510 a job failure is detected, block 512 directs the processor circuit 32 to move the addressed job file from the running jobs directory 405 back to the job files directory 313, so that the job may be subsequently executed by another available processor circuit. The processor circuit is then directed to block 518 below.

If no job failure is detected, block 514 directs the processor circuit 32 to determine whether the addressed job has been completed. To achieve this, block 514 directs the processor circuit 32 to examine the contents of the local/tmp/directory of the processor circuit associated with the addressed job, to determine whether a BLAST output text file has been stored therein, as discussed above in connection with block 420 of the BLAST execution routine.

If at block 514 it is determined that the job was successfully completed, block 516 directs the processor circuit 32 to compress and move the BLAST output file from the local/tmp/ directory on the available processor circuit running the BLAST analysis execution routine 400 to a completed BLAST results directory 515 in the storage medium 33.

Following execution of block 516 or block 512, or if at block 514 it was determined that the job is incomplete (but not failed at block 510), then block 518 directs the processor circuit 32 to determine whether each of the jobs listed in the running jobs directory 405 has been addressed at blocks 508 through 516 above. If not, the processor circuit is directed back to block 508 to address the next successive running job record as discussed above.

If all running jobs have been addressed, block 520 directs the processor circuit 32 to determine whether the job files directory 313 contains any job files (i.e., jobs which have not yet been executed). If so, the processor circuit 32 is directed back to block 502 to continue distributing jobs among the various processor circuits as discussed above.

Figure 7:
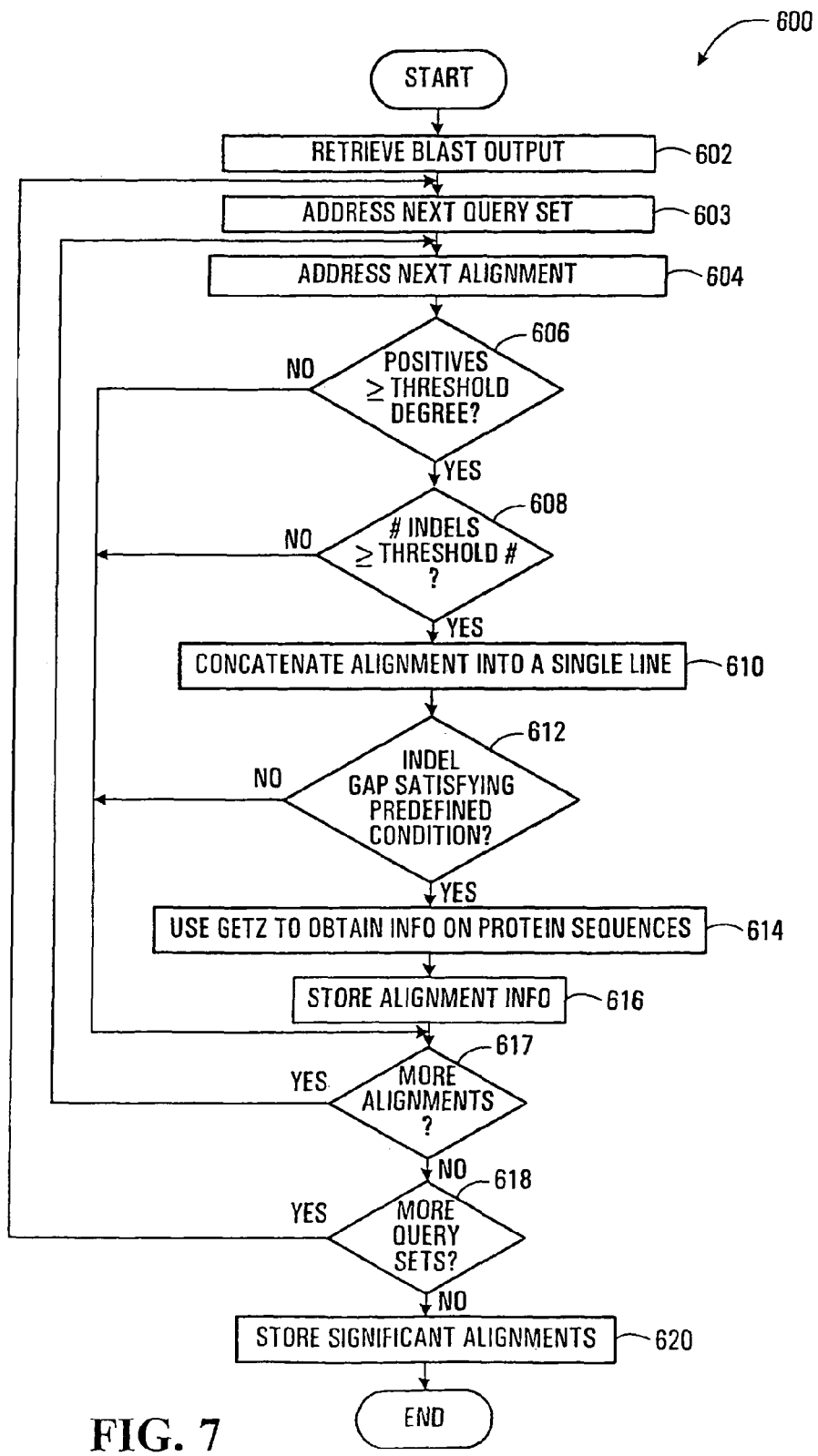

Referring to FIGS. 3 and 7, the significant indel identification routine is shown generally at 600 in FIG. 7. Generally, the significant indel identification routine configures any one of the available processor circuits shown in FIG. 3 to further analyze the BLAST alignment results (stored as BLAST output files) generated by the BLAST execution routine 400 and stored in the BLAST results directory 515 as discussed above in connection with block 516 of the BLAST distribution routine 500. In this embodiment, such further analysis of the BLAST output file (BLAST alignment results) involves identification of what are termed in this embodiment as significant indels. "Significance" of an indel is determined by pre-defined criteria, which in this embodiment include percentage of alignment identity and the number of consecutive amino acids comprising an indel.

Under the direction of the indel distribution routine 700 discussed below, the processor circuit 32 may effectively assign indel analysis tasks to each of the available processor circuits shown in FIG. 3, to cause such available processor circuits to execute the significant indel identification routine. For ease of understanding, therefore, the present routine is described as being executed by the "processor circuit", with the understanding that any one of the distributed processor circuits may execute is routine.

The significant indel identification routine 600 begins with a first block of codes 602, which directs the processor circuit to retrieve a BLAST output file stored in the blast output directory 515 in the storage medium 33.

Block 603 directs the processor circuit to address the next query set stored in the retrieved BLAST output file, commencing with the first such query set when block 603 is first executed. In this regard, it will be recalled that in the present embodiment, the BLAST output file includes 1000 such query sets, each query set including an identification of the query sequence, and identifications of aligned protein sequences having a substantial alignment identify with the query sequence, as located by the BLAST algorithm.

Block 604 then directs the processor circuit to address the next aligned protein sequence stored in the currently addressed query set of the retrieved BLAST output file, commencing with the first such aligned sequence when block 604 is first executed.

Block 606 then directs the processor circuit to determine whether the addressed aligned sequence has an alignment identity of greater than or equal to a threshold degree of alignment (which in this embodiment is 70%) with the query sequence of the currently addressed query set. If the addressed aligned sequence has less than the threshold degree of alignment, the processor circuit is effectively directed to discard the addressed aligned sequence, and is directed to block 617 below.

If the addressed aligned sequence has at least the threshold degree of alignment with the query sequence of the addressed query set, block 608 directs the processor circuit to determine whether the currently addressed aligned sequence has at least six gaps relative to the query sequence, each gap representing a single amino acid of the query sequence that has no corresponding amino acid at the corresponding location in the currently addressed aligned sequence, or vice versa. In this embodiment, this may be achieved by determining whether the "gap value" in the BLAST output file for the aligned sequence is greater than or equal to 6 (6 amino acid gaps anywhere in either protein sequence). If not, the processor circuit is effectively directed to discard the aligned sequence and is directed to block 617 below.

If the inquiry at block 608 is answered in the affirmative, blocks 610 and 612 direct the processor circuit to evaluate whether there is a significant indel in the aligned sequence. To achieve this, block 610 directs the processor circuit to concatenate the alignment into a single line of sequence, then block 612 directs the processor circuit to determine whether the currently addressed aligned sequence has at least one indel satisfying a predefined condition. In this embodiment, the predefined condition is a minimum length of the indel, which in this embodiment is a length of at least six contiguous amino acids. Alternatively, other suitable predefined conditions may be substituted, such as those discussed above in connection with the previous embodiment, for example. If the addressed aligned sequence does not have at least one indel satisfying the predefined condition, the processor circuit is effectively directed to discard the aligned sequence and to proceed to block 617 below.

Conversely, if the aligned sequence has at least one indel satisfying the predefined condition, block 614 directs the processor circuit to obtain additional information about the currently addressed query sequence and aligned sequence. To achieve this, block 614 directs the processor circuit to execute a routine called "getz", which obtains additional information about the pair of aligned protein sequences (such as organism name and protein type). Such information may be achieved by directing the processor circuit to query the sequence database 38, for example, although alternatively, other ways of obtaining such information may be substituted.

Block 616 then directs the processor circuit to locally store ("local/temp/directory") the additional information along with the corresponding alignment information in a local storage medium accessible by the processor circuit.

Block 617 then directs the processor circuit to determine whether the currently addressed query set includes any additional aligned protein sequences that have not yet been addressed at blocks 604 et seq. above, and if so, the processor circuit is directed back to block 604 to address the next successive aligned protein sequence of the currently addressed query set.

If no fisher aligned protein sequences in the currently addressed query set remain to be addressed, block 618 directs the processor circuit to determine whether the retrieved BLAST output file includes any additional query sets corresponding to additional respective query sequences, which have not yet been addressed at blocks 603 et seq. above. If so, the processor circuit is directed back to block 603 to address the next successive query set in the BLAST output file.

If no further query sets remain to be addressed, block 620 directs the processor circuit to store all of the alignment information stored above at block 616, in a consolidated text file, for subsequent retrieval by the processor circuit 32 shown in FIG. 3.

Figure 8:
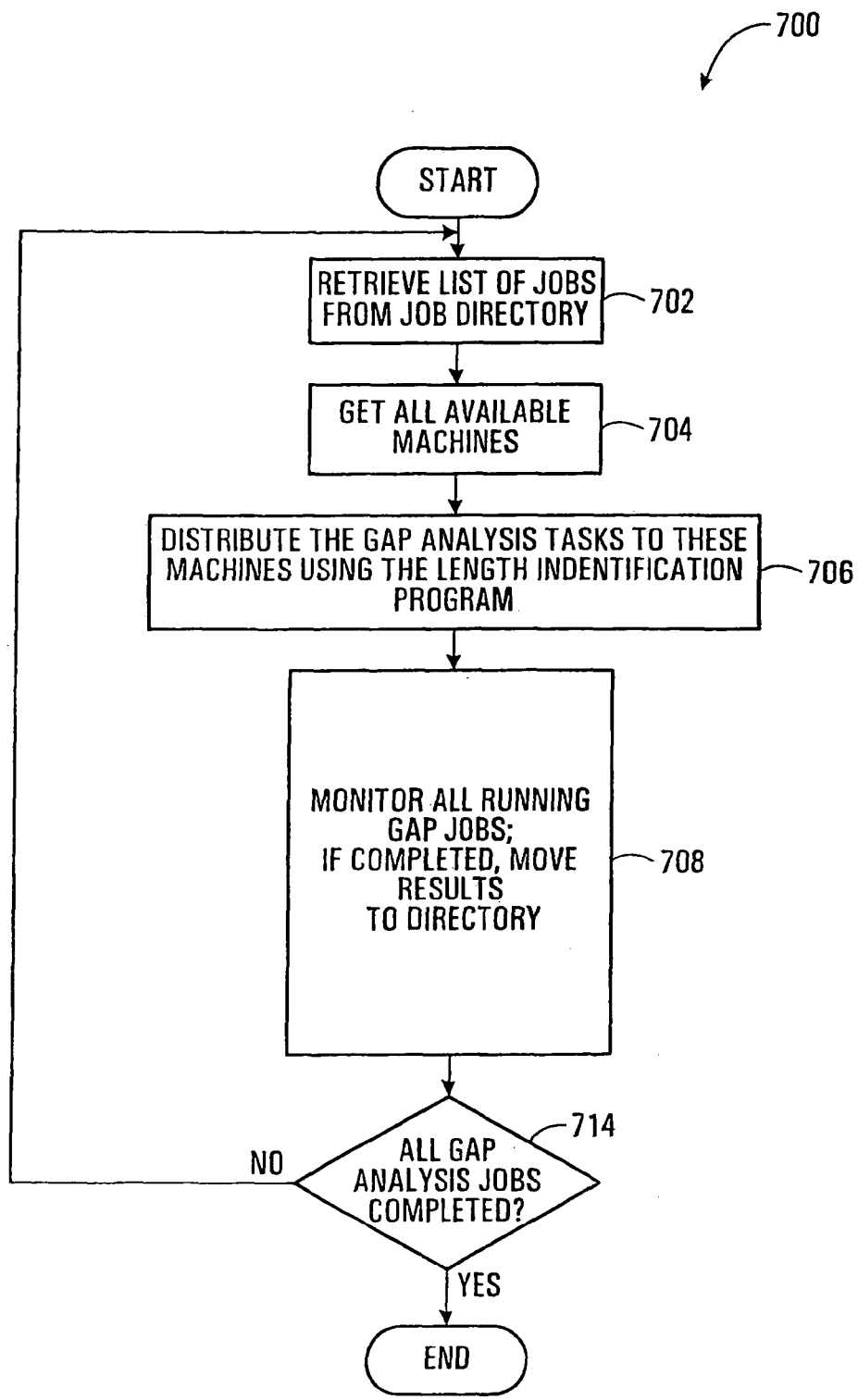

Referring to FIGS. 3 and 8, the significant indel analysis distribution routine is shown generally at 700 in FIG. 8. Generally, the significant indel analysis distribution routine directs the processor circuit 32 to distribute indel analysis jobs to any of the various available processor circuits shown in FIG. 3, for distributed execution of the significant indel identification routine 600 discussed above.

The significant indel analysis distribution routine 700 begins with a first block of codes 702 that directs the processor circuit 32 to retrieve a list of job files from BLAST results directory 515.

Block 704 then directs the processor circuit 32 to determine which of the various distributed processor Circuits shown in FIG. 3 are available for execution of the indel identification routine 600. This may be achieved by directing the processor circuit to communicate directly with the various distributed processor circuits, or alternatively, by communicating with a central network node, for example. In this embodiment, a processor circuit is considered to be available if it has a MIPS≧2000/equal to or better than a dual 1 GHz CPU and load averages of less than 2, although alternatively, other availability criteria may be substituted.

Block 706 then directs the processor circuit 32 to effectively distribute one significant indel identification job to each of the available processor circuits. Such distribution may occur in a manner similar to that described above in connection with block 506, for example, and upon distribution of an indel identification job to a processor circuit, the identification of that job is removed from the BLAST output directory 515.

Block 708 further directs the processor circuit 32 to monitor all significant indel identification jobs running on the available processor circuits. In this regard, block 708 directs the processor circuit 32 to check each individual available processor circuit to see if the significant indel identification routine (length polymorphism program) 600 for a given job was successfully executed. This determination may be achieved in a manner similar to that discussed above in connection with block 514, for example. If the job was not successfully completed, block 708 directs the processor circuit 32 to move the job back to the BLAST results directory 515 and clear the failed significant indel identification analysis job from the processor circuit in question. However, if the job was successfully executed, then block 708 directs the processor circuit 32 to move the stored indel analysis results from the local/tmp/directory on the available processor circuit to a completed significant indel analysis directory 713 in the storage medium 33.

Block 714 then directs the processor circuit 32 to determine whether the BLAST results directory 515 includes any further indel analysis jobs that have not yet been executed, and if so, the processor circuit is directed back to block 702 to continue distributing indel analysis jobs until all such jobs have been completed.

Referring to FIGS. 3 and 9, a partial data structure produced by the processor circuit under the direction of the significant indel analysis routine 600 is shown generally at 900 in FIG. 9. In this embodiment, the data structure 900 includes respective fields, including a field 902 for storing an identification of the first protein sequence; a field 904 for storing an identification of one of the first group of aligned protein sequences having at least the threshold degree of alignment with the first sequence and having at least one indel relative to the first sequence satisfying the predefined condition; a field 906 for storing a degree of alignment identity between the one of the first group of aligned sequences and the first sequence; and field 908 for storing indications of insertions or deletions of the one of the first group of aligned sequences relative to the first protein sequence. In at least some cases, the first protein sequence will represent a pathogen protein sequence, and therefore, in such cases, the field 902 stores an identification of a pathogen protein sequence.

As an example of the above mentioned method, significant indels have been identified in elongation factor-1α (EF-1α) from trypanosomatids and other protozoa. The results of this example are described in further detail below.

B) Protein Sequence Analysis Method—Identification of Drug Target Suitability Characteristics Sequences with an alignment identity of ≧70% and with gaps of four amino acids or greater may be stored together in a database for further structural analysis, for example to determine the structure and to determine frequency and type of amino acids surrounding predicted indels and alternatively to look at the region of the pathogen protein "unshielded", where the corresponding human protein is concealed or shielded by the indel (henceforth referred to as an "indel complementarity region"). The results of the alignments and subsequent indel analysis would also facilitate further functional and experimental analysis. Pathogen proteins may be further characterized to determine their role in the pathogens life in the host organism and importance for pathogen survival, reproduction or ability to cause disease in the host organism and therefore to decide whether or not the protein is a potential target. If the functional analysis reveals that the pathogen protein is "essential" whereby in the absence of function of the protein will result in death, lack of viability lack of pathogenicity, or incapability of reproduction of the pathogen in the host organism then it may be termed an "essential" protein. Alignments that satisfy the above criteria can be stored with their accompanying information in a database or data structure to be retrieved and further analyzed later.

The indel sequence, the indel complementarity region and overall protein sequence can be further analyzed based on secondary structure (PHD program—Rost, B. and Sander. C. (1993) J. Mol. Biol. 232(2):584-599; Rost, B. and Sander, C. (1993) Proc Natl Acad Sci USA 90(1-6):7558-62; Rost, B. and Sander, C. (1994) *Proteins,* 19(1):55-72; PSIPRED program—Jones, D. T. (1999) J. Mol. Biol. 292(2):195-202), whereby the conformation of a protein or peptide molecule with respect to nearest-neighbour amino acids is analyzed. Also the frequency and type of amino acids surrounding the predicted indels and the indel complementarity region can be determined. Furthermore, the tertiary and quaternary structure of the pathogen and host proteins can be compared to look for potential drug target sites on the pathogen protein that are not available on the corresponding host protein.

Molecular modeling of a protein structure can be performed using the SwissPDB Viewer package (Guex N. and Peitsch M C. (1997) *Electrophoresis* 18:2714-2723) combined with the Molecular Operation Environment (MOE) software package (Version 2001.01, Chemical Computing Group Inc., Montreal, Canada) as described below. Homology templates used for modeling can be retrieved from the Expasy server (www.expasy.ch) can provide the user with solved structures of the protein of interest or for similar proteins.

Example Characterization of Pathogenic EF-1α

Elongation factor-1α(EF-1α) from *Leishmania donovani* is a Src-homology 2 domain containing protein tyrosine phosphatase-1 (SHP-1) binding and activating protein. Persons skilled in the art would be able to prepare GST-SHP-1 construct, based on the expression and purification previously described by Jiao H. et al. ((1996) *Mol. Cell. Biol.* 16:6985-6992). cDNA encoding *L. donovani* EF-1α was PCR amplified, cloned and sequenced. The deduced amino acid sequence shows that the *leishmania* protein is shorter than mammalian EF-1α by a twelve amino acid deletion. In spite of this, the apparent molecular mass of *leishmania* EF-1α is higher than its mammalian counterpart. There is nearly complete sequence conservation amongst EF-1α proteins from trypanosomatids, when compared to mammalian EF-1α sequences. Consistent with this, the sub-cellular, distributions of *L. donovani* EF-1α and host EF-1α are strikingly different. In *leishmania*, the majority of EF-1α is Triton-X100-insoluble, whereas macrophage EF-1α is predominantly cytosolic. Infection of macrophages with *L. donovani* causes redistribution of host as well as pathogen EF-1α. In contrast to its predominant distribution in the Triton-insoluble fraction in promastigotes and amastigotes, *leishmania* EF-1α was essentially completely cytosolic in infected macrophages. In addition, infection results in farther redistribution of host EF-1α to the cytosol. Protein modeling shows discrete 3-dimensional structural differences between the proteins showing important structural differences between mammalian and trypanosomatid EF-1α and their role in the latter in pathogenesis.

Protein Function Analysis

To examine whether *leishmania* EF-1α associated with host SHP-1 in vivo, macrophages were infected with promastigotes for 14-16 hrs. Cytosolic fractions were then prepared from control and infected cells for immunoprecipitation of SHP-1. Immune complexes were separated by SDS-PAGE under non-reducing conditions followed by transfer to nitrocellulose. Immunoblot analysis carried out using anti-EF-1α showed that *leishmania* EF-1α associated with SHP-1 in vivo, whereas the association of host-EF-1α with host SHP-1 was minimal. These findings show that *leishmania* EF-1α is a selective SHP-1 binding protein in vivo during infection.

EF-1α was purified to near homogeneity from murine macrophages and from *leishmania* promastigotes. Binding assays performed using the purified proteins and GST-SHP-1 glutathione-sepharose beads showed that EF-1α from *leishmania* bound directly and selectively to SHP-1 as comparatively little binding of host EF-1α was detected. In contrast, both *leishmania* and macrophage EF-1α bound directly and with similar affinities to calmodulin, a known EF-1α binding protein. These findings show that the purified host EF-1α was functionally intact and confirmed that *leishmania* EF-1α is a selective SHP-1 binding protein.

Purified EF-1α proteins from both macrophages and *leishmania* were examined for their ability to modulate SHP-1 phosphatase activity in vitro. *Leishmania* EF-1α, but not its mammalian homologue, was capable of activating GST-SHP-1 in vitro.

Purified EF-1α proteins introduced into macrophages using the protein delivery system Profect-1 (Targeting System, Santee, Calif.) resulted in SHP-1 activation in vivo. In contrast, activation of SHP-1 was not observed when purified macrophage EF-1α or BSA were used as control proteins. Delivery of purified, native *leishmania* EF-1α, but not the corresponding host protein into cells blocked induction of iNOS expression in response to cell treatment with interferon-γ. Thus, *leishmania* EF-1α was able to recapitulate the deactivated phenotype of *leishmania*-infected macrophages. These results show that *leishmania* EF-1α is a selective activator of SHP-1 capable of inducing macrophage deactivation.

EF-1α from vacuole bound *leishmania* must cross two membranes (the parasite plasma membrane and the parasitophorous vacuole) to access cytosolic SHP-1. We have been able to detect EF-1α as a tyrosine phosphorylated protein in promastigote growth medium in the absence of parasite lysis indicating that it is exported in some manner. Furthermore, concentrated promastigote growth medium was able to activate SHP-1. When *leishmania* infected macrophages are subjected to selective lysis to preserve phagosome integrity, followed by immunoprecipitation of cytosolic SHP-1, EF-1α is identified in these complexes. Thus, these molecules do associate in vivo thereby providing an opportunity for activation of SHP-1. Our findings that the *leishmania* EF-1α is tyrosine phosphorylated and that the sequence contains two canonical ITIM motifs is consistent with the protein activity SHP-1 as a result of binding of tyrosine Phosphorylated ITIM motifs to SH2 domains of SHP-1.

The Sub-Cellular Distribution of *L. Donovani* EF-1α is Distinct from Macrophage EF-1α

The distinct molecular mass of *leishmania* EF-1α as compared to the corresponding host protein suggested potential functional differences. To investigate this further, the sub-cellular distribution of EF-1α in *L. donovani* promastigotes and macrophages was examined. Cytosolic; Triton-soluble and Triton-insoluble fractions were prepared from *L. donovani* promastigotes and macrophages, separated by SDS-PAGE, transferred to nitrocellulose and probed with anti-EF-1α. The results show that in *leishmania* promastigotes, the majority of EF-1α was in the Triton-insoluble fraction, whereas in macrophages, EF-1α was predominantly cytosolic. The lower molecular mass band in the *leishmania* Triton-insoluble fraction (Ti) is most likely a proteolytic degradation product of EF-1α.

Sera from patients with visceral leishmaniasis recognize *leishmania*, but not host EF-1α. The results show that *leishmania* EF-1α is structurally distinct from human EF-1α. EF-1α was immunoprecipitated from Trition X-100 lysates of *L. donovani* promastigotes using anti-EF-1α antibodies. Immune complexes were separated by SDS-PAGE under non-reduced conditions followed by transfer to nitrocellulose membranes. Immunoblot analysis was carried out using either anti-EF-1α, normal human sera or sera from visceral leishmaniasis patients. The results also indicate that *leishmania* EF-1α was recognized by sera from patients infected with *L. donovani*. Importantly, EF-1α immunoprecipitated from cells of the human mononuclear phagocytic cell line THP-1, was not recognized by sera from *L. donovani* infected patients. These findings show that the primary amino acid sequence differences between *leishmania* EF-1α compared with human EF-1α are sufficiently distinct that corresponding structural differences contribute to the formation of epitopes in the *leishmania* protein that are processed and recognized by the immune system. It should also be noted that EF-1α of *leishmania* is a closely spaced doublet when separated on SDS-PAGE under non-reduced conditions.

Leishmania Infection Alters the Subcellular Distribution of Both Macrophage and *leishmania* EF-1α

EF-1 ax is known to be involved in a variety of cellular processes in addition to regulation of protein synthesis [Condeelis J. (1995) *Trends Biochem. Sci.* 20:169-170; Kaur, K. J. and Ruben, L. (1994) *J. Biol. Chem.* 269:23045-23050; Murray J W. et al. (1996) *J. Cell Biol.* 135, 1309-1321; Ganatra J B. et al. (2000) *Am. J. Ophthalmol.* 129:1.66-172]. We examined the distribution of both host and *leishmania* EF-1α during macrophage infection. For infection, macrophages were incubated with *L. donovani* stationary phase promastigotes for 16 to 18 h at a parasite-to-cell ratio of approximately 10:1. This resulted in infection rates of >95% with approximately four to eight promastigotes per cell. To determine the sub-cellular distribution of EF-1α in non-infected and *L. donovani* infected macrophages, cytosolic, Triton-soluble and Triton-insoluble fractions were prepared as described in Experimental Procedures and analyzed for EF-1α by immunoblotting. In contrast to its predominant distribution in the Triton-insoluble fraction in promastigotes, *leishmania* EF-1α was principally cytosolic in infected macrophages. Simultaneously, infection of macrophages with *leishmania* resulted in a redistribution of host EF-1α to the cytosol, thereby increasing its overall abundance in this fraction. Similar results were obtained when cells were infected with *leishmania* amastigotes. The effect of *leishmania* infection on redistribution of EF-1α was specific as phagocytosis by macrophages of *Staphylococcus aureus* did not cause redistribution of host EF-1α.

Protein Structure Analysis—Molecular Modeling of EF-1α

Modeling of the structure of *leishmania* EF-1α was done using the SwissPDB Viewer package [Guex N. and Peitsch M C. (1997) *Electrophoresis* 18:2714-2723]. A homology template search was done in which the sequence of *leishmania* EF-1α in Fasta format was downloaded into the software environment of SwissPDB. The EF-1α sequence was then submitted to the Expasy server (www.expasy.ch) to search against the database of proteins of known structure. The server returned the sequence of *Saccharomyces cerevisiae* EF-1α (1G7CA) as a top homology search result. Three other PDB entries (1F60A, 1IJEA, 1IJFA) corresponding to EF-1α proteins from *S. cerevisiae* were also identified as possible modeling templates and were used for homology modeling of *L. donovani* EF-1α.

For homology modeling, the templates for 1G7C, 1F60A, 1IJEA, 1IJFA were downloaded from the ExPasy server and imported into SwissPDB program. The template backbones were superimposed by using "SwissPDB|Fit|Magic Fit" procedure. The structure of 1G7CA was used as a master template. To derive a preliminary structural estimate for EF-1α: from *L. donovani*, the templates for 1G7C, 1F60A, 1IJEA, 1IJFA were superimposed and the sequence of the *leishmania* protein was fitted into the composite using "SwissPDB|Fit|Raw Sequence" procedure. Consecutive use of procedures "SwissPDB|Fit|Magic Fit", "SwissPDB|Fit|Improve Fit" and "SwissPDB Fit|Best" allowed the predicted structure to be improved. In order to refine this preliminary structure further, the side chains and terminal chains had to be modeled (SwissPDB usually truncates terminal and irregular regions). This was done using the Molecular Operation Environment (MOE) software package (Version 2001.01, Chemical Computing Group, Inc., Montreal, Canada). The homology model of *leishmania* EF-1α (previously built by the SwissPDB-Viewer) was used as a template and the curated PDB file 1G7C from the PDB database provided with the MOE package was used as a second template. The 1G7C template from the curated PDB database was imported by command "MOE|File|Protein Database" and the sequence of *leishmania* EF-1α and its preliminary SwissPDB homology model were downloaded using option "MOE|File|Open". The MOE Sequence Editor was then used for iterative sequence alignment with Gonnet substitution matrix. Secondary structure elements were not used for the sequence alignment. The MOE command "Seq. Editor|Homology|Align" was used to perform the alignment. Homology modeling of *leishmania* EF-1α was then carried out with the highest degree of protein structure optimization. The previously derived SwissPDB model of the *leishmania* protein was used as a template. The final structure was derived as a Cartesian average of the top ten scored, non-minimized intermediate models. The estimated top ten homology models built for *leishmania* EF-1α were saved in MOE database*.mdb format to be viewed by the MOE database Viewer called by "MOE|Open|*.mdb". The final 3-D structure of the protein was averaged over the top ten scoring models.

Once the refined 3-D model of the EF-1α protein from *L. donovani* was created, the homology modeling procedure was repeated on a modeling template of EF-1α from *S. cerevisiae* (PDB file 1G7CA). The modeling routine was carried out in the exact same way as previously described for *L. donovani's* EF-1α with all numerical parameters the same. This step was taken in order to justify the accuracy of the homology model of *leishmania* EF-1α and to build its terminal chains not previously modeled by the SwissPDB Viewer. The homology model of the protein EF-1 ax from *L. donovani* created on the 1G7CA template by MOE resembled the SwissPDB model with very high accuracy. The two structures of the *leishmania* protein created by MOE on the templates of 1G7CA and of the SwissPDB model had a high degree of resemblance with a calculated RMSD between the two structures of 0.69A. Based upon this analysis, the 3D structure of EF-1α from *L. donovani* built using MOE on a template of the SwissPDB model was accepted as final. Lastly, since EF-1α proteins from *Mus musculus* and *Homo sapiens* share 99.8% identity and have 81.1% sequence identity with 1G7C, homology Modeling of these proteins was done in the same manner as for *L. donovani* EF-1α.

Cloning of L. Donovani EF-1α cDNA and Determination of the Deduced Amino Acid Sequence Alignment of EF-1α genes from *L. braziliensis, T. cruzi, T. brucei* and others revealed a high degree of conservation. PCR primers were designed based upon the sequence of the *L. braziliensis* gene and used to amplify the coding sequence of the *L. donovani* EF-1α gene from cDNA of *L. donovani* promastigotes. The predicted amino acid sequence of EF-1α of *L. donovani* was compared with other trypanosomatids (*T. biucei, T. cruzi*) and with the human sequence. The multiple alignment comparison showed that a high degree of homology extended through the complete sequence. The GTP-binding consensus motifs and the three lysine residues that are usually post-translationally modified were found to be conserved in *L. donovani*. Notably however, there were several important differences observed in the trypanosomatid sequences as compared to the human sequence. For example, it was remarkable to note at position 151-152 the replacement of glycine and valine in the human sequence with cysteines in the trypanosomatid sequences, suggesting possible differences in folding of the proteins. In addition, human EF-1α was found to contain twelve extra amino acids when compared with trypanosomatid EF-1α sequences. The protein sequence of *L. donovani* shows the presence of two previously unrecognized putative immunoreceptor tyrosine-based inhibitory motifs (ITIMs). These specialized motifs are known to be present in many signaling molecules with the capability of binding to Src homology 2 domains (SH2 domains) [Berg K L. et al. (1998) *Oncogene* 17:2535-2541; Frearson J A. and Alexander D R. (1997) *BioEssays* 19:417-427; Blery M. et al. (2000) *Hum. Immunol.* 61:51-64].

The molecular mass of trypanosomatid EF-1α was found to be higher than mammalian EF-1α. Initial immunoblot analysis of EF-1α in Triton X-100 cell lysates of *L. donovani* promastigotes and the human carcinoma cell line A431 showed that the apparent molecular size of EF-1α of *L. donovani* was distinctly higher than the human homolog. To determine whether this was a specific characteristic of the *leishmania* protein or a more general property of the trypanosomatid family of which *L. donovani* is a member, Triton X-100 cell lysates of several trypanosomatid and mammalian cell lines were separated on SDS-PAGE, transferred to nitrocellulose and probed with anti-EF-1α antibodies. The results show that the apparent molecular mass of EF-1α from trypanosomatids is hither than mammalian EF-1α. The apparent molecular size of EF-1α from trypanosomatids was found to be approximately 56 kDa as compared to 50 kDa for EF-1α of mammalian origin. The molecular mass of EF-1α did not change when Triton X-100 lysates of *L. donovani* promastigotes at different stages of growth (exponential and stationary phases) were analyzed by immunoblotting.

Analysis of Molecular Modeling of EF-1α

To model and analyze the 3-D structure of *leishmania* EF-1α, its amino acid sequence was scanned against the database of the proteins with known 3D structures. This analysis showed that *L. donovani* EF-0: has 75% identity with EF-1α from *S. cerevisiae*. The 3-D structure of *S. cerevisiae* EF-1α was previously determined experimentally (PDB entry 1G7C) [Andersen G R. et al. (2001) *Nat. Struct. Biol.* 8:531-534)] and was used as a template for *L. donovani* EF-1α protein modeling. The estimated degree of identity (above 75%) allowed for accurate modeling of *L. donovani* EF-1α: based upon the 1G7C template. The 3-D structure of the main body of *L. donovani* EF-1α was constructed by homology modeling and side chains were generated by averaging a number of computed models. Protein sequence alignment also showed that EF-1α from *S. cerevisiae* shares 77.3% sequence identity with EF-1α from *Mus musculus* and 77.3% with EF-1α from *Homo sapiens*. The 3-D structures for these proteins were also modeled and further refined based upon the template of 1G7C. Comparison of the models shows that the 3-D structures of EF-1α proteins from *S. cerevisiae, L. donovani, Mus musculu* and from *Homo sapiens* resemble each other closely. Without taking into account the differences in irregular C-terminal loop regions, the only notable difference in the structures of the human and *leishmania* proteins is attributed to an isolated hairpin fragment corresponding to the insertion of twelve amino acids in the *H. sapien's* protein sequence at position 214, that is missing from *L. donovani* EF-1α. The structure of this twelve amino acid fragment was identified as a hairpin motif comprised of two anti-parallel β strands each of which is four amino acids in length. *L. donovani* EF-1α has a proline residue at position 214 corresponding to point of insertion of the hairpin fold in the *H. sapien's* EF-1α. This proline likely functions to stabilize the backbone of *L. donovani* EF-1α by preserving local structural similarity with EF-1α from *H. sapiens*. However, this proline "stitching" at the point of the deletion in the 3-D structure of *L. donovani's* EF-10: is likely not able to compensate fully for the nearly 5.4A wide gap corresponding to the distance between top edges of the hairpin, and some distortions in flexible, irregular chains surrounding the deletion site in the *leishmania* protein may occur.

The cloning and characterization of EF-1α from *L. donovani* have now provided novel information to show clearly that the *leishmania* protein has unique properties that distinguish it from macrophage EF-1α. The deduced 449 amino acid sequence for the *leishmania* protein was observed to share identity of ≧90% with other known EF-1α proteins from trypanosomatids, whereas identity was found to be 75.5% with the human protein. Despite this high degree of overall protein sequence homology, important amino acid substitutions such as replacement of glycine and valine at positions 151-152 of the human sequence by cysteines in the *leishmania* sequence were found. In addition, a twelve amino acid deletion in the primary sequence of the *L. donovani* sequence was identified. Protein modeling predicts significant differences in 3-D structure when comparing the *leishmania* protein with the human homologue. *Leishmania* and mammalian EF-1α's were also observed to have distinct apparent molecular sizes and subcellular distributions. The results clearly show that the distinct molecular mass of *leishmania* EF-1α is a general property shared by homologues obtained from other trypanosomatids. Furthermore, the *leishmania* protein, but not its mammalian homologue binds to and activates SHP-1 These distinct properties are influenced by the differences in 3-D structure.

EF-1α is known to contain a large number of post-translational modifications, whose roles have not been established. Most notably, EF-1α is modified by methylation of lysine residues [Damen J E. et al. (1995) *J. Biol. Chem.* 270:23402-23408] and glycerolphosphoryl-ethanolamine additions [Stein R C. and Waterfield M D. (2000) Mol. *Med. Today* 6:347-357; Hoedemaeker F J. et al. (1999) *J. Mol. Biol.* 292: 763-770; Yohannan J. et al. (1999) *J. Biol. Chem.* 274:18769-18776] and the appropriate residues are present in the *L. donovani* protein. Sequence analysis of *L. donovani* EF-1α showed that the protein has two putative ITIM motifs (xxYAxV) that are conserved and analysis with 4G10 antibodies indicated that it is tyrosine phosphorylated. These specialized motifs are known to be present in many signaling molecules and have the potential to bind to SH2 domains [Berg K L. et al. (I 998) *Oncogene* 17:2535-2541; Frearson J A. and Alexander D R. (1997) *BioEssays* 19:417-427; Blery M. et al. (2000) *Hum. Immunol.* 61:51-64]. It has been shown that a phospholipase C-γl construct containing both SH2 and SH3 domains directly binds to EF-1α [Vanhaesebroeck B. et al. (1999) *Nat. Cell Biol.* 1:69-71]. These motifs account for the binding of *leishmania* EF-1α to SHP-1, whereas overall differences in 3-D structure account for why the mammalian homologue does not do so, in spite of the fact that it also contains the same motifs. The presence of antibodies against *leishmania* EF-1α (bit not the human homologue) in sera of patients with visceral leishmaniasis support further the conclusion that *leishmania* EF-1α is structurally distinct from host EF-1α.

Three-dimensional structure of EF-1α from *L. donovani* was modeled and compared with EF-1α of *H. sapiens*. In spite of the overall high degree of primary amino acid sequence similarity, a hairpin of twelve amino acids was modeled that was unique to the *H. sapiens* protein. To investigate functional significance of the indel (hairpin from the human form), its sequence -GWKVT$^{217}$RKDGNASGT- (SEQ ID NO: 4) (available from genBank) was searched against the PROSITE database that contains information about protein motifs with defined functions. This analysis showed that *H. sapien's* EF-1☐ contains potential consensus phosphorylation sites (PROSITE matches PS00005 and PS00006) for protein kinase C (Kishimoto A. et al. (1985) *J Biol. Chem.* 260:12492-12499) and casein kinase II (Pinna, L A. (1990) *Biochim. Biophys. Acta* 1054:267-284) at threonine$^{217}$ in the hairpin loop. These findings show that the hairpin loop present in EF-1☐ proteins from *H. sapiens* and other higher eukaryotes and missing in *L. donovani* EF-1☐, contributes to the experimentally observed differences in their function and subcellular distribution.

The crystal structure of EF-1α proteins from *S. cerevisiae* reveals the close proximity of the 20A long hairpin to the main body of the protein. Thus, the side chains of the hairpin form a complex network of hydrophobic and polar interactions involving the α-helix formed by amino acids 226-231, the β-strand formed by residues 233-236 and the low complexity region of amino acids 182-191 in the main body of the protein. For example, Glu$^{215}$ in the hairpin reaches a proximity of 2A with the side chain of Leu$^{184}$ in the main part of the protein implying the formation of hydrogen bonds between the residues. The homologue also shows these structural properties.

The remarkable absence of these twelve residues and the hairpin formed by them in the structure of *leishmania* EF-1α, provides the basis to design small molecule inhibitors that bind specifically to the regions of the *leishmania* protein otherwise shielded by the hairpin fragment in the *H. sapiens* protein. Specifically, the putatively "unshielded" region of *leishmania* EF-1α (contains several highly polar residues such as Asp$^{218}$, Glu$^{224}$, Met$^{222}$, Lys$^{187}$ and Arg$^{189}$ with their charged side chains pointed directly toward the predicted location of the missing hairpin. One or more of these residues are sites for drug attack. Conversely, the bulky amino acids, Trp$^{210}$, Phe$^{211}$, Trp$^{214}$ and Tyr$^{217}$ in the hairpin contribute to blocking an attacking reagent from reaching the corresponding structural region of the *Homo sapien's* homologue.

EF-1α may be selectively inactivated in *leishmania*, without interfering with the host EF-1α homolog, considering the essential requirement for EF-1α for survival and its role as a virulence factor. The absence of the hairpin structure from EF-1α sequences of other pathogenic trypanosomatids (e.g. *T. cruzi, T. brucei brucei* and *T. congolense*) and unrelated protozoa such as *Entameoba histolytica* and the other protozoans referred to herein, shows that such drugs will have affect on an important range of widely prevalent pathogens.

The results show that *leishmania* infection causes the redistribution of both host and pathogen EF-1α. During infection, *leishmania* EF-1α became principally cytosolic in nature in contrast to its predominant Triton-insoluble distribution in extracellular promastigotes. Simultaneously, infection of macrophages with *leishmania* resulted in the redistribution of host EF-1α to the cytosol, thereby increasing its overall abundance in this cellular compartment. The results show that *leishmania* EF-1α is principally cytosolic in infected cells. Similar results were obtained when cells were infected with either promastigotes or amastigotes, indicating that redistribution of *leishmania* EF-1α is not due to parasite transformation during infection. Redistribution of host and pathogen EF-1α during *leishmania* infection appears to be specific for *L. donovani* infection, since redistribution of host EF-1α was not observed when cells had ingested fixed *S. aureus*.

C) Targeted Drug Development

Once the structure of the pathogen protein and particularly the pathogen specific region is characterized as described above. Bioinformatic programs may be used to screen the conformations of known small molecules for potential fit within the indel complementarity region or the indel itself depending on whether the indel occurs on the host (then target indel complementarity region) or on the pathogen (then target the indel region itself). Furthermore, potential binding moieties may be incubated in solution with the target protein crystals, and the complementarity region or the indel region may be once more defined by crystallography to determine fit of the therapeutic or drug molecule. If the structure of a target pathogen protein is determined by molecular modeling or by X-ray crystallography, then a person skilled in the art would be able to then design a three-dimensional shape of a putative binding moiety (e.g. see: U.S. Pat. Nos. 6,127,524 and 6,168, 928.).

EXAMPLE

*Leishmainia* EF-1α

The "unshielded" region of pathogenic EF-1α, which is concealed by a hairpin loop in the human protein, contains several highly polar residues with exposed side chains. Small molecules and peptides may be designed (using conventional modeling techniques and available software) to specifically bind to this unshielded region. Such a specific binding moiety will have a binding site containing one or more binding elements, which may be one or more chemical groups capable of forming a hydrogen or ionic bond or participate in a hydrophobic interaction with one or more contact residues in the unshielded region of EF-1α. Preferably, two or more such bonds and/or interactions will exist. The aforementioned bonds may exist between a group on the specific binding moiety and atoms in the polypeptide backbone or in an amino acid side chain at the unshielded region, in the presence of or the absence of water molecules between the binding moiety and the unshielded region. Preferably, the distance between a binding element in the moiety and a contact residue will be 5 Angstroms or less, more preferably from 1-4 or from 2-3 Angstroms. Preferably, a contact residue will be selected from one or more amino acids in the unshielded region, capable of forming a hydrogen bond or which have polar side chains, preferably amino acids corresponding to one or more of Asp$^{218\ or\ 221}$, GLu$^{186\ or\ 224}$ Met$^{222}$, Lys$^{187}$ and Arg$^{189}$ of *leishmania* EF-1α. The specific binding moiety may have the capacity of binding other regions of EF-1α by hydrophobic or polar interactions, particularly with the regions corresponding to amino acids 182-191 and 226-236 of yeast EF-1α (such as Leu$^{184}$) or amino acids 158-168, 186-194, and 215-224 of *leishmania* EF-1α. The atomic coordinates of EF-1α as determined by molecular modeling or by X-ray crystallography may be used to then design a three-dimensional shape of a putative binding moiety (e.g. see: U.S. Pat. Nos. 6,127,524 and 6,168,928).

Characterization of EF-1α as described above shows that antibodies specific for the pathogenic variant may be generated. In addition to small molecules/peptides, specific binding moieties according to this invention may be antibodies or antibody fragments specific for the unshielded region of pathogen EF-1α or which otherwise specifically bind to the pathogen form. Antibodies and antibody fragments may be generated by well known techniques.

The specific binding moieties described above may cause a change in function of pathogenic EF-1α (e.g. by affecting SHP-1 binding or by affecting EF-1α's role in protein translation) or the moiety may simply bind with specificity to the pathogenic form. In the latter instance, the moiety may be used as a targeting ligand in assays for the label or pathogenic form (e.g. with a radiolabel or other moiety which facilitates detection) or as a targeting ligand for therapeutic moieties that themselves bring about an affect on the pathogenic protein.

Anti-pathogenic EF-1α Antibodies. Antibodies towards the three-dimensional surface differences of the *leishmania* EF-1α protein will have efficacy-since they may interfere with either one or both of two important functions that enable the pathogen to infect humans. The first function is the fundamental role of EF-1α in pathogen protein translation. The second is the role of EF-1α as a virulence factor.

The three-dimensional model of the *leishmania* identifies the peptide sequences that are normally concealed (indel complementarity region) by the hairpin loop (indel) present on human EF-1α. Using publicly available protein structure visualization programs, short peptide sequences derived from *leishmania* EF-1α may be selected for development of an antibody using standard techniques for monoclonal antibody (mAb) production. Three sequences are:

1. amino acids 215-224 TLLDALDMLE (SEQ ID NO: 1)
2. amino acids 186-194 EKVRFIPIS (SEQ ID NO: 2)
3. amino acids 158-168 KTVTYAQSRYD (SEQ ID NO: 3)

Specific mAbs may be used to investigate the importance of the indel complementarity region on *leishmania* EF-1α using independent assay systems which determine: (1) whether they interfere with the function of *leishmania* EF-1α in in vitro translation assays, (2) whether they block the interaction of *leishmania* EF-1α with SHP-1 in vitro, and (3) whether upon introduction into *leishmania* infected macrophages they affect parasite viability.

Recombinant peptides/proteins to target EF-1α for proteolysis. Given the differential epitopes displayed on the otherwise highly conserved EF-1α proteins of *leishmania* and humans, this strategy involves the construction of a moiety that binds and neutralizes the exposed epitope of *leishmania* EF-1α In the case of a moiety that binds but does not inhibit the protein synthesis function or the virulence factor properties of EF-1α, an alternative strategy utilizing macrophage intracellular trafficking may be used to destroy the pathogen EF-1α protein.

Examples of two strategies are ones which utilize aspects of the ubiquitin pathway responsible for the majority of protein turnover within a eukaryotic cell. Typically ubiquitin is ligated to proteins targeted for destruction and serves as a marker for transport to lysosomes and subsequent proteolysis. Both strategies take advantage of the capacity of a synthetic indel peptide based upon the human EF-1α sequence to selectively bind the exposed epitopes available on the surface of *leishmania* EF-1α, but not on the human protein. The synthetic indel will contain either a terminal signal for ubiquitination, or the protein sequence for ubiquitin.

Chimeric EF-1α Indel

One of the ubiquitination complexes that has been well characterized governs the turnover of IκBα, the inhibitor of NFκB. NFκB controls expression of many genes associated with inflammation. The protein IκBα is recruited to the ubiquitination complex by virtue of a 10 amino acid sequence (hereafter referred to as 'recruitment peptide') that is phosphorylated in response to inflammatory signals [Sakamoto K M. et al. (2001) PNAS 98(15):8554-9]. Thus, at the onset of inflammation upon infection, the inhibitor to inflammatory gene expression is destroyed, and upregulation of NF-κB controlled genes expression occurs and the recruitment peptide is activated. The recruitment peptide may be added onto the C-terminal of a specific binding moiety as described above which may be the actual 12 amino acid indel, joined by an amino acid to the recruitment peptide. The chimeric indel may be delivered to *leishmania* infected macrophages using either liposomes or a protein targeting reagent such as Profect-1™. *Leishmania* viability in macrophages may be monitored and compared to control treated cells (introduction of an irrelevant peptide sequence of identical size and linked to the recruitment peptide).

A second strategy uses expression of a recombinant peptide comprised of an N-terminal ubiquitin sequence and a C-terminal indel peptide. The C-terminal sequence of ubiquitin may be mutated from a glycine to an alanine to prevent cleavage of the ubiquitin protein [Tellam J. et al., (2001) Journal of Biological Chemistry 276(36):33353-60]. The cDNA for human ubiquitin may be amplified by PCR from a human cDNA library using specific 5' and 3' oligonucleotide primers to facilitate cloning of the ubiquitin gene into the prokaryotic expression vector pBlueBac4.5/V5-His Transfer Vector (Invitrogen), permitting expression in an insect cell line. The 3' oligonucleotide will contain the appropriate mutation to convert the glycine$^{76}$ codon to alanine. The nucleic acid coding sequence for the indel may be synthesized as two complementary oligonucleotides and ligated in frame with the ubiquitin gene to allow for expression of a recombinant ubiquitin-indel protein. Purified ubiquitin-indel protein may be delivered to *leishmania* infected macrophages as described above for chimeric proteins, followed by assessment of parasite survival.

X-Ray Crystallography

Persons skilled in the art would know how to express pure EF-1α in a recombinant system such as baculovirus and how to purified by affinity chromatography. A full length *L. donovani* EF-1α gene may be PCR amplified using oligonucleotide primers that contain restriction endonuclease sites to facilitate ligation into a baculovirus expression vector. A baculovirus system is preferable over prokaryotic expression systems [Button, L L. et al. (1993) Gene 134(1):75-81], because the EF-1α protein appears to undergo post-translational modifications, including methylation of lysine residues and glycerolphosphoryl-ethanolamine additions, not possible in bacteria. Human EF-1α may be cloned, expressed, and purified using this methodology.

The *L. donovani* EF-1α-EK-His coding sequence may be similarly sub-cloned into an expression vector such as pBlueBac4.5 (Invitrogen) and cotransfected with the Bac-N-Blue vector (Invitrogen) into Sf9 insect cells and the viral supernatant harvested at day three. Plaque assays may be performed to isolate pure virus that will be screened by PCR to identify recombinant virus. High titer virus stocks can be prepared and used to infect Sf9 insect cells for high level expression of *L. donovani* EF-1α [Button, L L. et al. (1993) Gene 134(1):75-81]. Cell lysates may be prepared and the EF-1α purified by affinity chromatography using ProBond columns (Invitrogen). After elution, EF-1α may be treated with enterokinase (enteropeptidase) (New England Biolabs) to remove the His tag, purified by FPLC gel exclusion chromatography and used for functional analysis. Affinity purified, baculovirus-expressed EF-1α may be incubated with GST-SHP-1 to examine its ability to bind to and activate the enzyme by phosphatase assay as described above. Synthetic phosphopeptides derived from the primary sequence of the two ITIMs of EF-1α, including five amino acids on either side of each, may be biotin conjugated and used to bind to and activate SHP-1 in vitro. These peptides may be compared with peptides in which tyrosine has been replaced by phenylalanine. The peptides may also be employed to compete with full length EF-1α for binding to SHP-1. PCR-based, site-directed mutagenesis as done previously [Button, L L. et al. (1993) Gene 134(1):75-81] may be used to produce full length protein in which either one or both tyrosines have been changed to phenylalanine to abolish SHP-1 binding.

Crystals of *leishmania* and human EF-10α may be grown following known protocols for yeast EF-1α a crystallization. Crystals of *leishmania* and human EF-1α may be grown by the hanging drop method, for example by combining equal volumes (2 µl) of the protein stock and mother liquor (e.g. 20% polyethylene glycol 8000, 0.1 M cacodylate, pH 6.5) at room temperature. Crystals may be subjected to vitrification in 30% polyethylene glycol 8000, 0.1 M cacodylate, pH 6.5 and 15% glycerol using liquid propane. Diffraction data may be collected, for example by using a Mar345 Image Plate detector with osmic mirrors mounted on a Rigaku RU-200 rotating anode x-ray generator. Data may be processed using HKL programs. Molecular replacement may be performed using CCP4 software, and subsequent refinement of the model may be done using the CNS program. An alternative expression system for the synthesis of recombinant proteins in *leishmania* may also be used [Joshi P B. et al. (1995) Gene 156(1):145-9; Laban A. and D F. Wirth (1989) PNAS 86(23): 9119-23; LeBowitz J H. et al. (1990) PNAS 87(24):9736-40; Kelly J M. et al. (1992) Nucleic Acids Research 20(15):3963-9], followed by purification and x-ray crystallography.

Bioinformatic programs may be used to screen the conformations of known small molecules for potential fit within the indel complementarity region of *leishmania* EF-1α [Ooms F. (200) Current Medicinal Chemistry 7(2):141-58; Kurogi, Y. and O. F. Guner (2001) Current Medicinal Chemistry 8(9): 1035-55; Gradler U. et al. (2001) Journal of Molecular Biology 306(3):4557-67; Aronov A M. et al. (2000) Biochemistry 39(16):4684-91]. Potential binding moieties nay be incubated in solution with EF-1α protein crystals, and the complementarity region once more defined by crystallography to determine fit of the therapeutic molecule.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

TABLE 1

Pair wise percentage residue identity between sequences of 1EF-α protein from 4 organisms.

|  | EF1α | EF11_HU | 1G7C.A | AAH0406 |
|---|---|---|---|---|
| EF-1α (*Leishmania donovani*) | 100.0 | 75.5 | 75.0 | 75.5 |
| EF11_HUMAN (*Homo sapiens*) | 77.7 | 100.0 | 81.1 | 99.8 |
| 1G7C.A (*Saccharomyces Cerevisiae*) | 73.5 | 77.3 | 100.0 | 77.3 |
| AAH0406 (*Mus musculus*) | 77.7 | 99.8 | 81.1 | 100.0 |

What is claimed is:

1. A method of protein sequence analysis, the method comprising:
   a) identifying, from among a first group of aligned protein sequences having at least a threshold degree of alignment with a first protein sequence, a second group of at least one of said aligned sequences having a host-pathogen relationship to each other, wherein,
      i) when the first protein sequence is a pathogen protein, at least one of said first group of aligned protein sequences comprises a protein sequence of a host organism to the pathogen,
      or
      ii) when the first protein sequence is a host protein, at least one of said first group of aligned protein sequences comprises a protein sequence of a pathogen to the host;
   and wherein the identifying is performed by a computer programmed to execute an analysis routine for performing said identifying;
   b) storing the second group of aligned sequences in a user accessible storage medium;
   c) identifying an INDEL that differs between the host protein and the pathogen protein as a potential drug target; and
   d) storing a third group of aligned sequences having both a host-pathogen relationship to each other and a potential INDEL drug target in a user accessible storage medium.

2. The method of claim 1 wherein said predefined condition comprises a minimum length of said at least one INDEL.

3. The method of claim 2 wherein said minimum length comprises a minimum length of at least four contiguous amino acids.

4. The method of claim 1 wherein said predefined condition comprises a maximum length of said at least one INDEL.

5. The method of claim 4 wherein said maximum length comprises a maximum length of 50 contiguous amino acids.

6. The method of claim 1 wherein said predefined condition comprises a predefined range of length of said at least one INDEL.

7. The method of claim 6 wherein said predefined range comprises a range of four to 50 contiguous amino acids.

8. The method of claim 1 further comprising comparing a plurality of protein sequences to said first protein sequence to identify said first group of aligned protein sequences having at least said threshold degree of alignment with said first protein sequence.

9. The method of claim 8 wherein said threshold degree of alignment is at least 70% alignment between each of said aligned protein sequences and said first protein sequence.

10. The method of claim 9 wherein said threshold degree of alignment is at least 80% alignment between each of said aligned protein sequences and said first protein sequence.

11. The method of claim 10 wherein said threshold degree of alignment is at least 90% alignment between each of said aligned protein sequences and said first protein sequence.

12. The method of claim 1 further comprising successively selecting each one of a plurality of protein sequences as said first protein sequence, and repeating said identifying for said each one of said plurality of protein sequences.

13. A method of protein sequence analysis, the method comprising:
   a) inputting into a computer, specifically programmed to execute a modeling routine, identifications of aligned protein sequences at least some of which have at least a threshold degree of alignment between a first protein sequence and a second protein sequence, and have at least one INDEL relative to said first protein sequence and said second protein sequence satisfying a predefined condition; wherein,
  i) when the first protein sequence is a pathogen protein, at least one of said first group of aligned protein sequences comprises a protein sequence of a host organism to the pathogen,
  or
  ii) when the first protein sequence is a host protein, at least one of said first group of aligned protein sequences comprises a protein sequence of a pathogen to the host;
b) identifying drug target suitability characteristics of a region of a pathogen protein in response to said aligned sequences using said modeling routine; and
c) storing identified drug target suitability characteristics in a user accessible storage medium.

14. The method of claim 13 wherein said predefined condition comprises a minimum length of said at least one INDEL.

15. The method of claim 14 wherein said minimum length comprises a minimum length of at least four contiguous amino acids.

16. The method of claim 13 wherein said predefined condition comprises a maximum length of said at least one INDEL.

17. The method of claim 16 wherein said maximum length comprises a maximum length of 50 contiguous amino acids.

18. The method of claim 13 wherein said predefined condition comprises a predefined range of length of said at least one INDEL.

19. The method of claim 18 wherein said predefined range comprises a range of four to 50 contiguous amino acids.

20. The method of claim 13 further comprising generating said identifications of said aligned protein sequences.

21. The method of claim 20 wherein generating comprises comparing a plurality of protein sequences to said pathogen protein sequence or said host protein sequence to identify said aligned protein sequences having at least said threshold degree of alignment with said pathogen protein sequence or said host protein sequence.

22. The method of claim 13 or claim 21 wherein said threshold degree of alignment is at least 70% alignment between each of said host protein sequences and said pathogen protein sequences.

23. The method of claim 22 wherein said threshold degree of alignment is at least 80% alignment between each of said host protein sequences and said pathogen protein sequences.

24. The method of claim 23 wherein said threshold degree of alignment is at least 90% alignment between each of said host protein sequences and said pathogen protein sequences.

25. The method of claim 13 further comprising storing said drug target suitability characteristics in association with aligned sequences.

26. The method of claim 13 wherein identifying said characteristics of said aligned sequences comprises, for each of said aligned sequences, identifying characteristics of said at least one INDEL and a complementarity region thereof.

27. The method of claim 26 wherein identifying characteristics of said at least one INDEL and said complementarity region comprises one or more of the following: identifying secondary structure of said pathogen protein sequence and said host protein sequences; identifying tertiary structure of said pathogen protein sequence and said host protein sequences; identifying quaternary structure of said pathogen protein sequence and said host protein sequences; and performing functional analysis of said pathogen protein.

28. The method of claim 27 further comprising identifying a moiety capable of binding to a target region of said pathogen protein sequence.

29. A method of protein sequence analysis, the method comprising:
a) identifying, from among a first group of aligned protein sequences having at least a threshold degree of alignment with a first protein sequence, a second group of at least one of said aligned sequences having a host-pathogen relationship to each other, wherein,
  i) when the first protein sequence is a pathogen protein, at least one of said first group of aligned protein sequences comprises a protein sequence of a host organism to the pathogen,
  or
  ii) when the first protein sequence is a host protein, at least one of said first group of aligned protein sequences comprises a protein sequence of a pathogen to the host;
and wherein the identifying is performed by a computer programmed to execute an analysis routine for performing said identifying;
b) displaying the second group of aligned sequences on a user interface; and
c) identifying an INDEL that differs between the host protein and the pathogen protein as a potential drug target; and
d) storing a third group of aligned sequences having both a host-pathogen relationship to each other and a potential INDEL drug target in a user accessible storage medium.

30. A method of protein sequence analysis, the method comprising:
a) inputting into a computer, specifically programmed to execute a modeling routine, identifications of aligned protein sequences at least some of which have at least a threshold degree of alignment between a first protein sequence and a second protein sequence, and have at least one INDEL relative to said first protein sequence and said second protein sequence satisfying a predefined condition; wherein,
  i) when the first protein sequence is a pathogen protein, at least one of said first group of aligned protein sequences comprises a protein sequence of a host organism to the pathogen,
  or
  ii) when the first protein sequence is a host protein, at least one of said first group of aligned protein sequences comprises a protein sequence of a pathogen to the host;
b) identifying drug target suitability characteristics of a region of a pathogen protein sequence in response to said aligned sequences using said modeling routine; and
c) displaying identified drug target suitability characteristics on a user interface.

* * * * *

SEQUENCE LISTING

```
<160> NUMBER OF SEQ ID NOS: 7

<210> SEQ ID NO 1
<211> LENGTH: 10
<212> TYPE: PRT
<213> ORGANISM: Leishmania

<400> SEQUENCE: 1

Thr Leu Leu Asp Ala Leu Asp Met Leu Glu
1               5                   10

<210> SEQ ID NO 2
<211> LENGTH: 9
<212> TYPE: PRT
<213> ORGANISM: Leishmania

<400> SEQUENCE: 2

Glu Lys Val Arg Phe Ile Pro Ile Ser
1               5

<210> SEQ ID NO 3
<211> LENGTH: 11
<212> TYPE: PRT
<213> ORGANISM: Leishmania

<400> SEQUENCE: 3

Lys Thr Val Thr Tyr Ala Gln Ser Arg Tyr Asp
1               5                   10

<210> SEQ ID NO 4
<211> LENGTH: 14
<212> TYPE: PRT
<213> ORGANISM: Homo sapiens
```

<400> SEQUENCE: 4

Gly Trp Lys Val Thr Arg Lys Asp Gly Asn Ala Ser Gly Thr
1               5                   10

<210> SEQ ID NO 5
<211> LENGTH: 432
<212> TYPE: PRT
<213> ORGANISM: Homo sapiens

<400> SEQUENCE: 5

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Ser
                20                  25                  30

Ser Ile Asp Lys Arg Thr Ile Glu Lys Phe Glu Lys Glu Thr Ala Glu
            35                  40                  45

Met Gly Lys Gly Ser Phe Lys Tyr Gly Trp Val Leu Asp Lys Leu Lys
        50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Thr Asp Ala Pro Gly His Arg
                85                  90                  95

Asp Phe Ile Lys Asn Met Ile Thr Gly Thr Ser Gln Ala Asp Cys Ala
            100                 105                 110

Val Pro Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
210                 215                 220

Gly Thr Met Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Ser Val Pro Val Gly Arg Val Glu Thr Gly Ile Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Gly Glu Ala Leu Pro
290                 295                 300

Gly Asp Ser Val Gly Phe His Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile

```
                355                 360                 365
Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Ala Glu Ser Phe Ser
                405                 410                 415

Asp Tyr Pro Pro Leu Gly Arg Phe Ala Val Arg Asp Met Arg His Thr
                420                 425                 430

<210> SEQ ID NO 6
<211> LENGTH: 432
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (4)..(431)
<223> OTHER INFORMATION: Xaa = Any Amino Acid.

<400> SEQUENCE: 6

Met Gly Lys Xaa Lys Xaa His Xaa Asn Xaa Val Val Xaa Gly His Val
1               5                   10                  15

Asp Xaa Gly Lys Ser Thr Xaa Thr Gly His Leu Ile Tyr Lys Cys Xaa
            20                  25                  30

Xaa Ile Asp Lys Arg Thr Ile Glu Lys Phe Glu Lys Glu Xaa Ala Glu
        35                  40                  45

Met Gly Lys Xaa Ser Phe Lys Tyr Xaa Trp Val Leu Asp Lys Leu Lys
    50                  55                  60

Ala Glu Arg Glu Arg Gly Ile Thr Ile Asp Ile Xaa Leu Trp Lys Phe
65                  70                  75                  80

Glu Xaa Xaa Lys Xaa Xaa Xaa Thr Ile Xaa Asp Ala Pro Gly His Arg
                85                  90                  95

Asp Phe Ile Lys Asn Met Ile Thr Gly Thr Ser Gln Ala Asp Xaa Ala
                100                 105                 110

Xaa Xaa Xaa Xaa Xaa Xaa Xaa Gly Xaa Phe Glu Ala Gly Xaa Ser
            115                 120                 125

Lys Xaa Gly Gln Thr Arg Glu His Ala Leu Leu Ala Xaa Thr Leu Gly
130                 135                 140

Val Lys Gln Xaa Xaa Val Xaa Xaa Asn Lys Met Asp Xaa Xaa Xaa Xaa
145                 150                 155                 160

Xaa Tyr Ser Gln Xaa Arg Tyr Glu Glu Ile Xaa Lys Glu Val Xaa Thr
                165                 170                 175

Tyr Xaa Lys Xaa Xaa Gly Tyr Asn Pro Xaa Xaa Val Xaa Phe Xaa Pro
            180                 185                 190

Ile Ser Gly Trp Xaa Gly Xaa Asn Met Xaa Xaa Xaa Ser Xaa Xaa Met
            195                 200                 205

Xaa Trp Xaa Lys Xaa Xaa Xaa Xaa Xaa Xaa Xaa Xaa Xaa Xaa Xaa Xaa
            210                 215                 220

Gly Xaa Xaa Leu Leu Xaa Ala Leu Asp Xaa Xaa Xaa Xaa Xaa Xaa Arg
225                 230                 235                 240

Pro Xaa Asp Lys Pro Xaa Xaa Xaa Pro Xaa Xaa Asp Val Tyr Lys Ile
                245                 250                 255

Gly Gly Ile Gly Xaa Val Pro Val Gly Arg Val Glu Thr Gly Ile Xaa
                260                 265                 270

Lys Pro Gly Xaa Val Val Thr Phe Ala Pro Xaa Asn Val Thr Thr Glu
```

```
                    275                 280                 285
Val Lys Ser Xaa Glu Met His His Glu Xaa Leu Xaa Glu Ala Xaa Pro
        290                 295                 300
Gly Asp Xaa Val Gly Phe Xaa Val Lys Asn Val Ser Val Lys Asp Xaa
305                 310                 315                 320
Arg Arg Gly Asn Val Xaa Gly Xaa Ser Lys Asn Asp Pro Xaa Xaa Glu
                325                 330                 335
Xaa Ala Xaa Phe Thr Ala Gln Val Ile Xaa Leu Asn His Pro Gly Gln
            340                 345                 350
Ile Ser Xaa Gly Tyr Ala Pro Val Leu Asp Cys His Thr Xaa His Ile
        355                 360                 365
Ala Cys Xaa Phe Xaa Xaa Xaa Xaa Lys Ile Asp Arg Arg Ser Gly
    370                 375                 380
Lys Xaa Xaa Glu Xaa Xaa Pro Lys Xaa Xaa Lys Ser Gly Asp Ala Ala
385                 390                 395                 400
Ile Val Xaa Met Val Pro Xaa Lys Pro Met Cys Xaa Glu Xaa Phe Xaa
                405                 410                 415
Asp Tyr Pro Pro Leu Gly Arg Phe Ala Val Arg Asp Met Arg Xaa Thr
            420                 425                 430

<210> SEQ ID NO 7
<211> LENGTH: 419
<212> TYPE: PRT
<213> ORGANISM: Leishmania braziliensis

<400> SEQUENCE: 7

Met Gly Lys Asp Lys Val His Met Asn Leu Val Val Gly His Val
1               5                   10                  15

Asp Ala Gly Lys Ser Thr Ala Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Ala Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Ser Pro Lys Ser Val Phe Thr Ile Ile Asp Ala Pro Gly His Arg
                85                  90                  95

Asp Phe Ile Lys Asn Met Ile Thr Gly Thr Ser Gln Ala Asp Ala Ala
            100                 105                 110

Ile Leu Met Ile Asp Ser Thr Gln Gly Gly Phe Glu Ala Gly Val Ser
        115                 120                 125

Lys Asp Gly Gln Thr Arg Glu His Ala Leu Leu Ala Phe Thr Leu Gly
    130                 135                 140

Val Lys Gln Met Val Val Cys Cys Asn Lys Met Asp Asp Lys Thr Val
145                 150                 155                 160

Gln Tyr Ser Gln Ala Arg Tyr Glu Glu Ile Ser Lys Glu Val Gly Thr
                165                 170                 175

Tyr Leu Lys Arg Val Gly Tyr Asn Pro Glu Lys Val Arg Phe Ile Pro
            180                 185                 190

Ile Ser Gly Trp Gln Gly Asp Asn Met Ile Asp Lys Ser Glu Ser Met
        195                 200                 205

Ala Trp Tyr Lys Gly Pro Thr Leu Leu Asp Ala Leu Asp Met Leu Ala
    210                 215                 220

Gly Ala Val Arg Pro Val Asp Lys Pro Gly Ala Ala Pro Ala Asp Val
```

-continued

```
225             230             235             240
Tyr Lys Ile Gly Gly Ile Gly Thr Val Pro Val Gly Arg Val Glu Thr
                245             250             255

Gly Ile Met Lys Pro Gly Asp Val Val Thr Phe Ala Pro Ala Asn Val
                260             265             270

Thr Thr Glu Val Lys Ser Ile Glu Met His His Glu Gln Leu Ala Glu
        275             280             285

Ala Val Pro Gly Asp Asn Val Gly Phe Asn Val Lys Asn Val Ser Val
    290             295             300

Lys Asp Ile Arg Arg Gly Asn Val Trp Gly Asn Ser Lys Asn Asp Pro
305             310             315             320

Ala Glu Glu Pro Ala Asp Phe Thr Ala Gln Val Ile Val Leu Asn His
                325             330             335

Pro Gly Gln Ile Ser Asn Gly Tyr Ala Pro Val Leu Asp Cys His Thr
                340             345             350

Ser His Ile Ala Cys Arg Phe Gly Thr Ile Glu Ser Lys Ile Asp Arg
                355             360             365

Arg Ser Gly Lys Asp Val Glu Lys Asn Pro Lys Ala Ile Lys Ser Gly
        370             375             380

Asp Ala Ala Ile Val Lys Met Val Pro Gln Lys Pro Met Cys Val Glu
385             390             395             400

Val Phe Asn Asp Tyr Pro Pro Leu Gly Arg Phe Ala Val Arg Asp Met
                405             410             415

Arg Arg Thr
```